US006921295B2

(12) United States Patent
Sommer et al.

(10) Patent No.: US 6,921,295 B2
(45) Date of Patent: Jul. 26, 2005

(54) MEDICAL LEAD EXTENSION AND CONNECTION SYSTEM

(75) Inventors: John L. Sommer, Coon Rapids, MN (US); Terrell M. Williams, Brooklyn Park, MN (US)

(73) Assignee: Medtronic, Inc., Minneapolis, MN (US)

( * ) Notice: Subject to any disclaimer, the term of this patent is extended or adjusted under 35 U.S.C. 154(b) by 130 days.

(21) Appl. No.: 10/331,895

(22) Filed: Dec. 30, 2002

(65) Prior Publication Data

US 2003/0143895 A1 Jul. 31, 2003

Related U.S. Application Data

(63) Continuation-in-part of application No. 09/838,814, filed on Apr. 19, 2001, now Pat. No. 6,705,900.

(51) Int. Cl.[7] .............................................. H01R 24/04
(52) U.S. Cl. ..................................................... 439/668
(58) Field of Search .............................. 439/668, 359, 439/281, 814, 271, 810, 361

(56) References Cited

U.S. PATENT DOCUMENTS

| | | | |
|---|---|---|---|
| 442,807 A | 12/1890 | Hatcher | |
| 3,649,367 A | 3/1972 | Purdy | |
| 4,411,277 A | 10/1983 | Dickhudt | |
| 4,466,441 A | 8/1984 | Skubitz et al. | |
| 4,583,543 A | 4/1986 | Peers-Trevarton | |
| 4,628,934 A | * 12/1986 | Pohndorf et al. | 607/27 |
| 4,740,170 A | 4/1988 | Lee et al. | |
| 5,000,177 A | 3/1991 | Hoffmann et al. | |
| 5,007,864 A | 4/1991 | Stutz | |
| 5,050,602 A | 9/1991 | Osypka | |
| 5,060,649 A | * 10/1991 | Hocherl et al. | 607/37 |
| 5,076,270 A | 12/1991 | Stutz | |
| 5,324,311 A | 6/1994 | Acken | |
| 5,328,442 A | 7/1994 | Levine | |
| 5,374,279 A | 12/1994 | Duffin et al. | |
| 5,376,206 A | * 12/1994 | Maurer et al. | 156/242 |
| 5,413,508 A | * 5/1995 | Obara | 439/729 |
| 5,439,391 A | 8/1995 | McEtchin et al. | |
| 5,679,026 A | 10/1997 | Fain et al. | |
| 5,697,804 A | 12/1997 | Froberg et al. | |
| 5,760,341 A | 6/1998 | Laske et al. | |
| 5,766,042 A | 6/1998 | Ries et al. | |
| 5,843,141 A | 12/1998 | Bischoff et al. | |
| 5,871,528 A | 2/1999 | Camps et al. | 607/119 |
| 6,006,135 A | 12/1999 | Kast et al. | |
| 6,044,302 A | 3/2000 | Persuitti et al. | |
| 6,192,279 B1 | 2/2001 | Barreras, Sr. et al. | 607/117 |

FOREIGN PATENT DOCUMENTS

| | | |
|---|---|---|
| EP | 0 587 379 A2 | 3/1994 |
| WO | WO 00/64535 | 11/2000 |
| WO | WO 01/80941 A2 | 11/2001 |
| WO | WO 02/068050 A1 | 9/2002 |

OTHER PUBLICATIONS

Medtronic Model 5866–45 Sizing Sleeve Technical Manual, Jan. 2002.
Medtronic Model 6925 Sizing Sleeve Kit Technical Manual, Oct. 1996.
Medtronic Model 6920 Sizing Sleeve Kit Technical Manual, Jan. 1997.

* cited by examiner

*Primary Examiner*—Chandrika Prasad
(74) *Attorney, Agent, or Firm*—Michael C. Soldner; Girma Wolde-Michael

(57) ABSTRACT

A system for implanting a medical electrical lead includes an elongated lead body and a relatively non-compliant lead extension joined to a proximal end of the proximal portion of the lead body. The lead body includes a plurality of connector rings positioned about a proximal portion of the lead body. The lead extension includes a plurality of temporary contact surfaces and a plurality of conductors wherein each conductor joins a temporary contact surface to a corresponding connector ring.

26 Claims, 21 Drawing Sheets

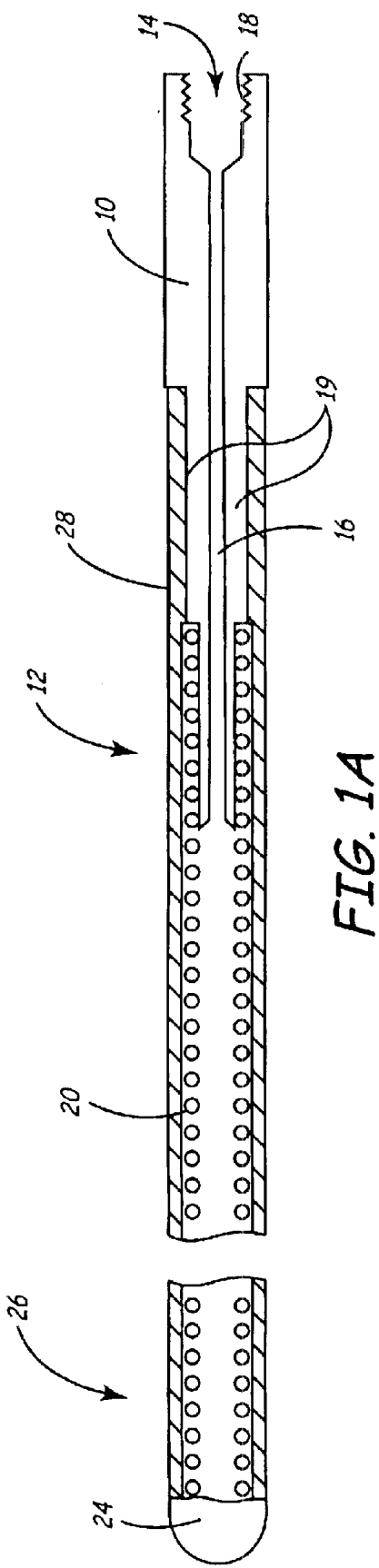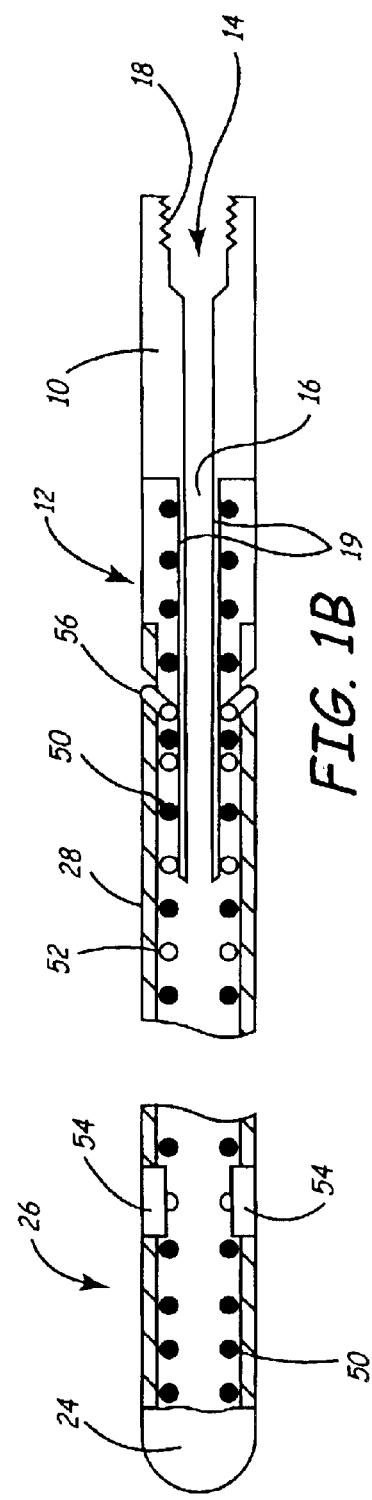

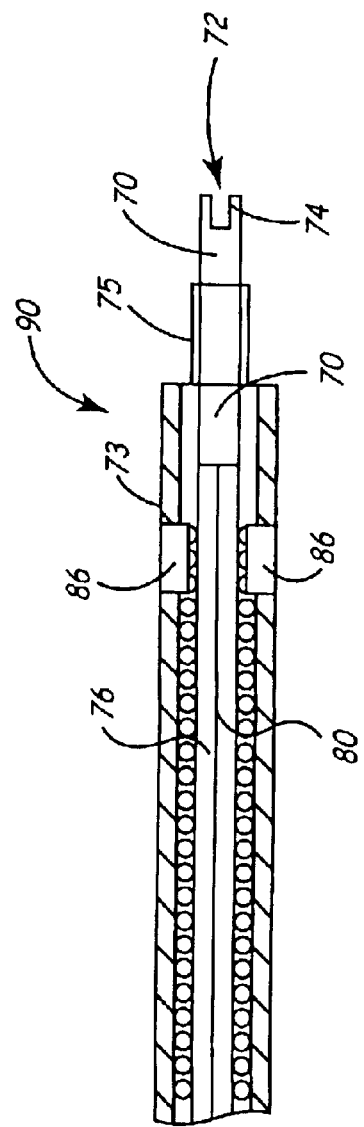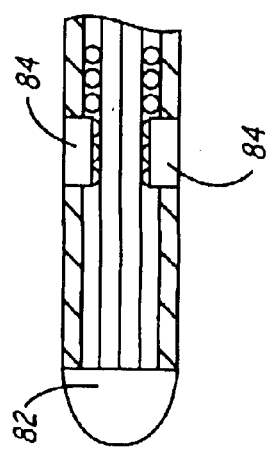
FIG. 1C

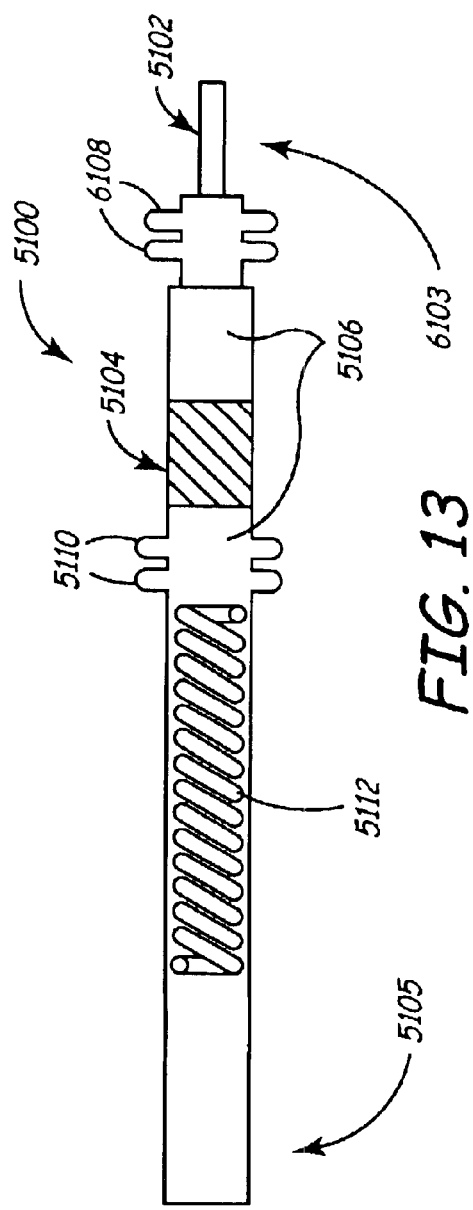
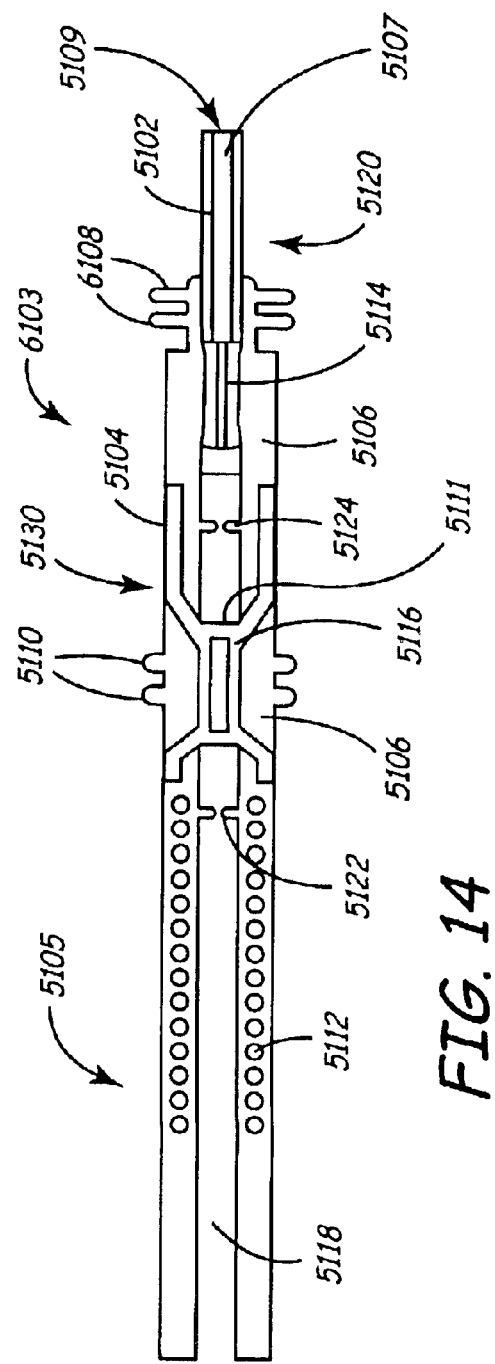

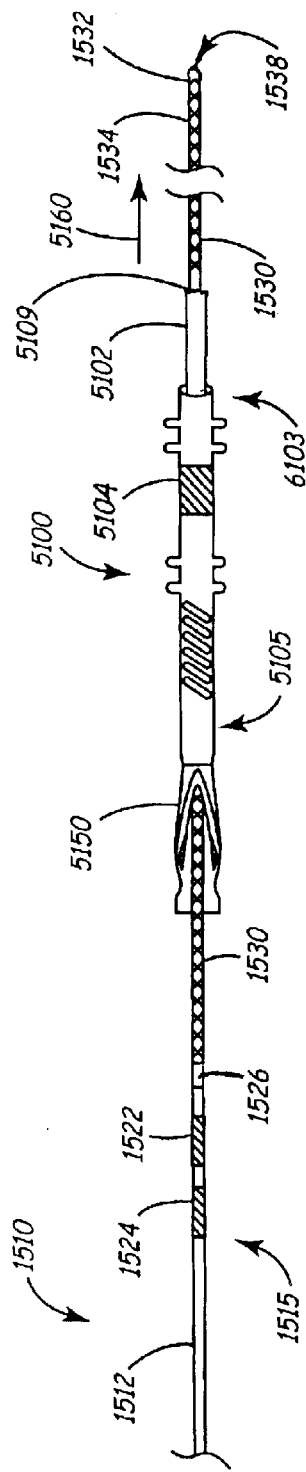
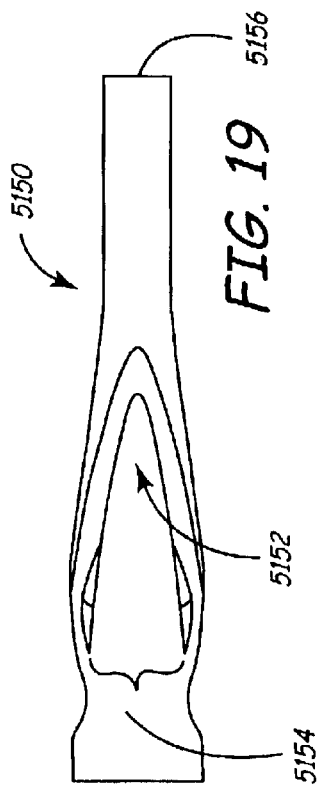
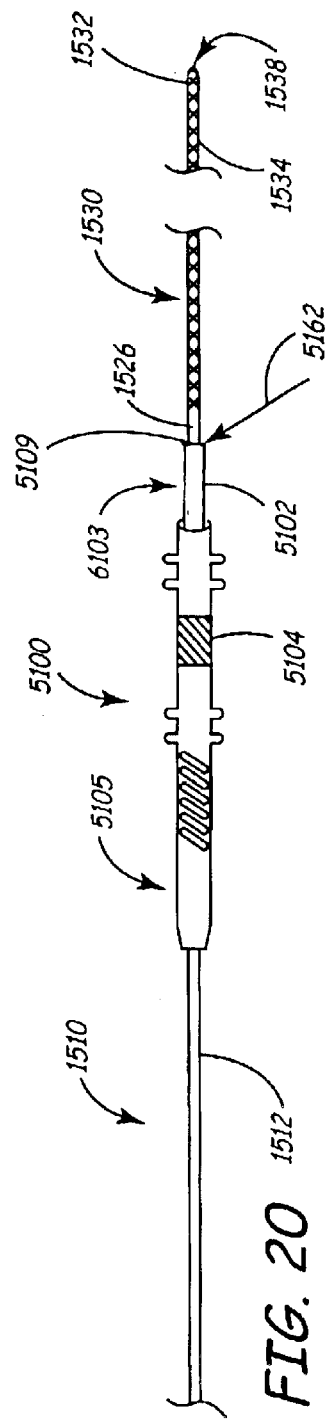
FIG. 18
FIG. 19
FIG. 20

MEDICAL LEAD EXTENSION AND CONNECTION SYSTEM

PRIORITY CLAIM

This application is a continuation-in-part of U.S. patent application Ser. No. 09/838,814, filed Apr. 19, 2001, now U.S. Pat. No. 6,705,900 entitled "Lead Up-Sizing Sleeve," which is incorporated herein by reference in its entirety.

FIELD OF THE INVENTION

The present invention relates generally to means for implanting medical electrical leads and, more specifically, to a system for electrically connecting a lead for stimulation therapy.

BACKGROUND OF THE INVENTION

Cardiac stimulation devices, including implantable cardiac pacemakers and implantable cardioverter defibrillators (ICDs), are electrically connected to the heart by at least one cardiac lead. Cardiac leads may be introduced transvenously and advanced through a venous pathway to a cardiac implantation site. For example, endocardial leads are commonly used to provide an electrical pathway between a pacemaker or ICD, connected to the proximal end of the lead, and one or more electrodes at the distal end of the lead that are in contact with endocardial tissue, typically within a right heart chamber. In such a manner, electrical pulses emitted by the pacemaker or ICD travel through the endocardial lead and stimulate the heart. Cardiac signals arising from the heart may be received by the lead electrodes and carried back to the device by the endocardial lead.

Transvenous leads may also be used for providing an electrical pathway to the left chambers of the heart. A transvenous lead may be advanced into the coronary sinus and further into the cardiac veins for stimulating the left atrial or left ventricular epicardial tissue and for sensing cardiac signals. It is desirable to advance coronary sinus leads deep into the cardiac veins in order to effectively stimulate and sense in the left ventricle.

When transvenous leads are implanted with the use of a guide catheter, some difficulties arise pertaining to the leads' electrical connectors. One difficulty arises when electrical testing must be performed at the time of implant. When transvenous leads are implanted it is common practice to test the position of the leads' electrodes for efficacy and efficiency of pacing, sensing and/or defibrillation. If the length of a lead is not sufficiently longer than that of a guiding catheter used to implant the lead, the lead's connector may be covered up by the guide catheter that is pulled back, proximally, to exposed the lead's electrodes; thus, connections cannot be made at the connector for electrical testing. Another difficulty arises if the lead connector assembly is sized to fit a standard device connector port. Such connectors generally have a larger diameter than the lead body so that a guiding catheter having a lumen sized for the lead body cannot be removed over these connectors. Pacemakers and ICDs are typically provided with connector ports conforming to an industry standard size. For example, an IS-1 connector port provides a 3.2 mm in-line electrical connector bore for receiving an IS-1 electrical lead connector of the type generally used to couple to cardiac pacing and sensing electrodes.

BRIEF DESCRIPTION OF THE DRAWINGS

FIG. 1A is a side cutaway view of an exemplary unipolar lead connector of the type that may be employed with the current inventive system.

FIG. 1B is a side cutaway view of an exemplary bipolar lead connector of the type that may be employed with the current inventive system.

FIG. 1C is a side cutaway view of yet another exemplary bipolar lead connector of the type that may be employed with the current inventive system.

FIG. 13 is a plan view of one embodiment of a connector sleeve assembly that may be used in conjunction with the lead of FIG. 11.

FIG. 14 is a, side, cut-away view of the connector sleeve assembly of FIG. 13.

FIG. 18 is a plan view illustrating a method of inserting the lead of FIG. 11 into the connector sleeve assembly of FIG. 13.

FIG. 19 is a plan view of a lead introducer used to aid in the insertion of a lead into a connector sleeve assembly.

FIG. 20 is a plan view of one embodiment of a lead engaged within a connector sleeve assembly.

DETAILED DESCRIPTION OF THE INVENTION

Figure 2A:
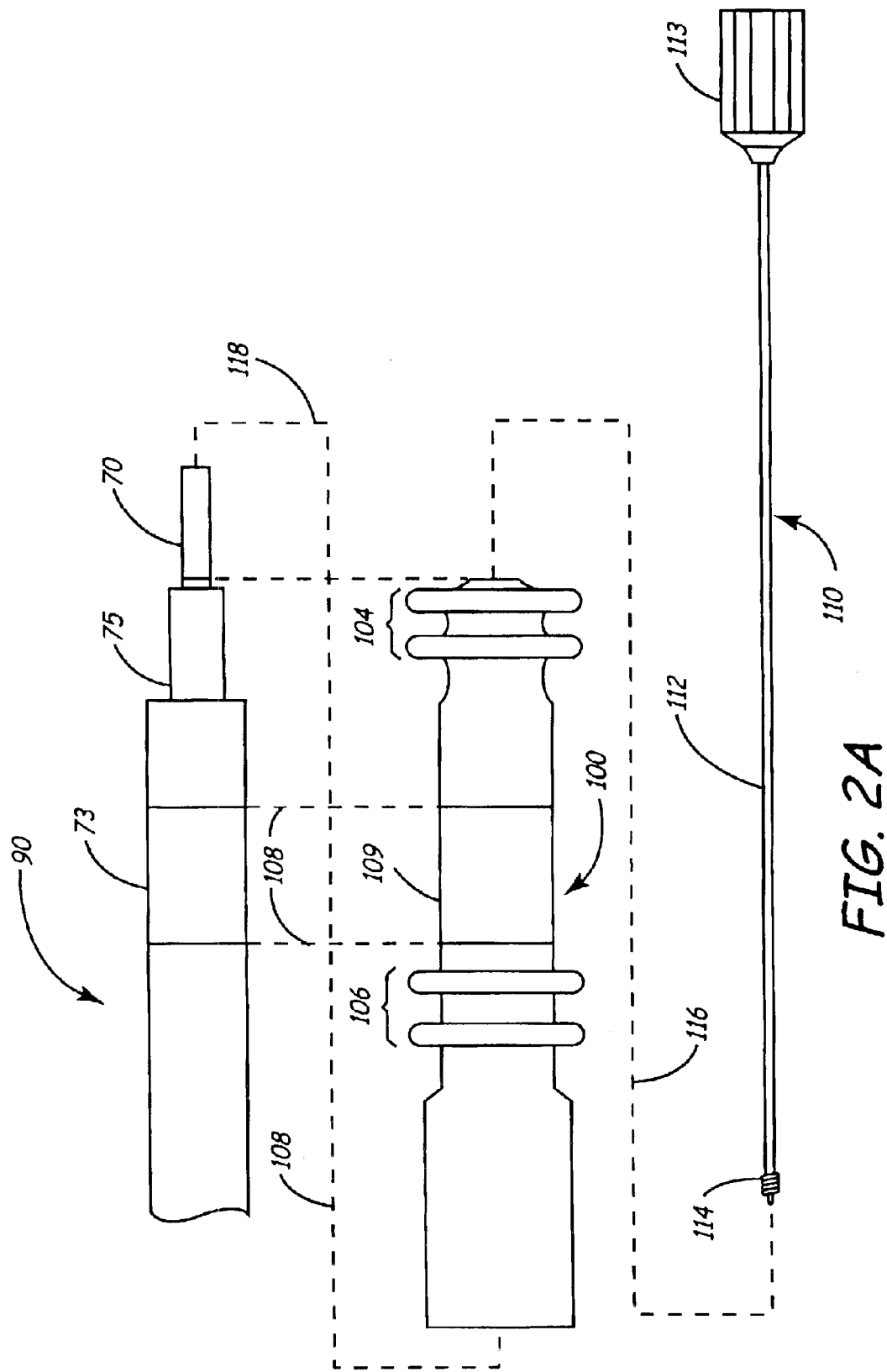
FIG. 2A is a plan view of one embodiment of an upsizing sleeve according to the current invention.

FIG. 1A is a side cutaway view of an exemplary unipolar lead connector of the type that may be employed with the current inventive system. The lead includes a connector pin 10 at the proximal end of the lead. In this view, the connector pin has substantially the same diameter as the lead body 12, although this is not necessary. Connector pin has an opening 14 that extends to inner lumen 16. A portion 18 of inner lumen 16 may be threaded.

Connector pin 10 couples to conductive member 19 that extends into lumen 16 and is electrically and mechanically coupled to at least one conductor 20. In FIG. 1A, conductor 20 is a conductive coil that extends the length of the lead body 12 to a tip electrode 24 at the lead body distal tip 26. In other embodiments, conductor 20 may take the form of a single-filar or multi-filar stranded conductor.

Lead body further includes an insulative jacket 28 that may be formed of a biocompatible polymer such as polyurethane or silicone. It may be noted that the lead of FIG. 1A is merely exemplary, and many other leads may be employed with the current invention. For example, a lead without an inner lumen extending within lead body 12 may be utilized. Alternatively, having multiple inner lumens may likewise be utilized.

FIG. 1B is a side cutaway view of an exemplary bipolar lead connector of the type that may be employed with the current inventive system. In FIG. 1B, elements that are similar to those shown in FIG. 1A are labeled with like designators. The lead of FIG. 1B includes a connector pin 10 that couples to conductive member 19. Conductive member 19 is electrically and mechanically coupled to an insulated coiled conductor 50. This conductor 50 extends the length of lead body 12 and is coupled at the distal tip 26 to tip electrode 24. A second insulated coiled conductor 52 is also provided to couple ring electrode 54 at the lead distal end to ring connector 56. In another embodiment, the conductors may be single or multi-filar stranded conductors.

FIG. 1C is a side cutaway view of yet another exemplary bipolar lead connector of the type that may be employed with the current inventive system. In this embodiment, a connector pin 70 is shown having an opening 72 that includes an inner, threaded surface 74. A portion of the connector pin is shown surrounded by an insulative sleeve 75 which may be formed of a polymer. This insulative sleeve electrically isolates pin from a connector ring 73, and provides additional structural support. The connector pin, which may have dimensions conforming to an IS-1 or another standard, extends within an inner lumen 76 of the lead body 12. This inner lumen houses a stranded conductor 80 such as shown in commonly-assigned U.S. Pat. No. 5,760,341 that is electrically coupled to tip electrode 82. The conductor 80 may be a single or multi-filar stranded conductor, or in a different embodiment, may be a coiled conductor. A second, coiled conductor 84 electrically couples ring electrode 86 to connector ring 73. It may be noted that although the connector pin 70 of this design may be of a dimension that corresponds to a standard such as an IS-1 connector pin standard, the overall lead dimensions of the proximal end 90 of the lead do not necessarily conform to any standard.

As discussed above, the lead configurations shown in FIGS. 1A, 1B, and 1C have small connector profiles. Therefore, a guide catheter used to place the leads during an implant procedure may be readily withdrawn over the connector pin without having to split or slit the catheter body. However, the connector pin 70 and the proximal end 90 of the lead body do not conform to a connector standard such as IS-1, making connection to a standard device connector block difficult. The upsizing sleeve of the current invention is provided as a means for facilitating this connection so that a specialized device connector block is not needed.

FIG. 2A is a plan view of one embodiment of an upsizing sleeve 100 according to the current invention. This upsizing sleeve is a generally tubular member having an inner lumen (not shown in FIG. 2) that is adapted to receive the proximal end of a lead such as the lead shown in FIG. 1C. The inner lumen of the upsizing sleeve is slightly larger than the outer diameter of proximal end 90 of the lead. For example, the proximal end 90 of the lead of FIG. 1C may be adapted to fit within the inner lumen as indicated by dashed line 102 such that the lead body forms a press fit with the surface defined by the lumen. The upsizing sleeve is adapted to conform to a standard configuration such as an IS-1 standard.

Upsizing sleeve is shown to include two sets of exterior sealing rings 104 and 106 adapted to sealingly engage with the connector port of a device such as pacemaker or defibrillator. Upsizing sleeve further includes a conductive ring member 109 adapted to electrically couple to connector ring 73 of the lead, as shown by dashed lines 108 in a manner to be discussed further below. Conductive ring member 109 is further adapted to mechanically and electrically couple to a set screw within the device connector to thereby couple ring connector 73 to a medical device in a manner dictated by the IS-1 connector standard. Sealing rings and the portions of upsizing sleeves surrounding conductive ring member 109 may be formed of one or more polymer structures such as polyurethane or silicone in a manner to be discussed further below.

Because of the relatively tight press-fit between the proximal end 90 of the lead and the upsizing sleeve 100, a pull-wire device 110 may be provided to aid in the insertion process. One embodiment of the pull-wire device 110 includes a rigid pull-wire 112 and a handle 113. The rigid pull-wire 112 may include a threaded distal end 114, which is inserted through the inner lumen of upsizing sleeve 100, as shown by dashed line 116. The threads of threaded distal end 114 are then positioned to engage threaded surface 74 (FIG. 1C) of the connector pin 70, as shown by dashed line 118. This allows the pull-wire 112 to rigidly engage the proximal end 90 of the lead so that the lead may be pulled through the inner lumen of the upsizing sleeve 100.

Although FIG. 2A shows pull-wire 112 including threaded distal end 114 to engage a lead, other coupling means could be provided to coupled to the lead, including a spring-loaded clip, or a plug to form a press-fit with opening 72.

Figure 2B:
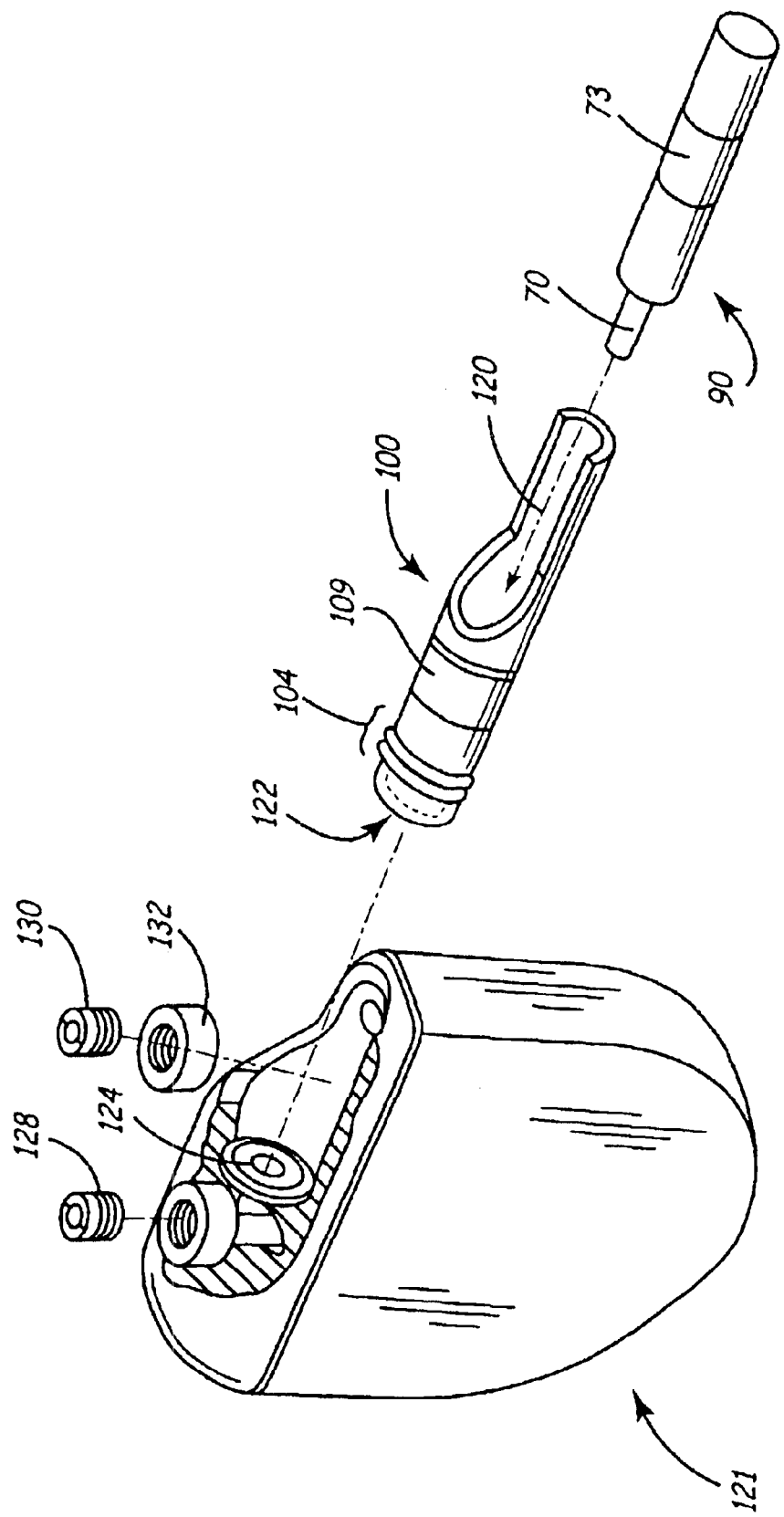
FIG. 2B is a perspective view illustrating the manner in which the inventive up-sizing sleeve may be used to couple a lead to a medical device.

FIG. 2B is a perspective view illustrating the manner in which the inventive up-sizing sleeve may be used to couple a lead to a medical device. The proximal end 90 of a lead such as shown in FIG. 1C includes a connector pin 70 and connector ring 73. This lead may be inserted into the inner lumen 120 of sleeve 100 so that connector ring 73 forms a press fit with conductive ring member 109, with connector pin 70 extending through the proximal end 122 of the sleeve. Connector pin is adapted to be received by port 124 of the medical device 121, which is further maintained by set-screw 128. A second set-screw 130 and washer 132 is provided to form a connection with conductive ring member 109.

Figure 3:
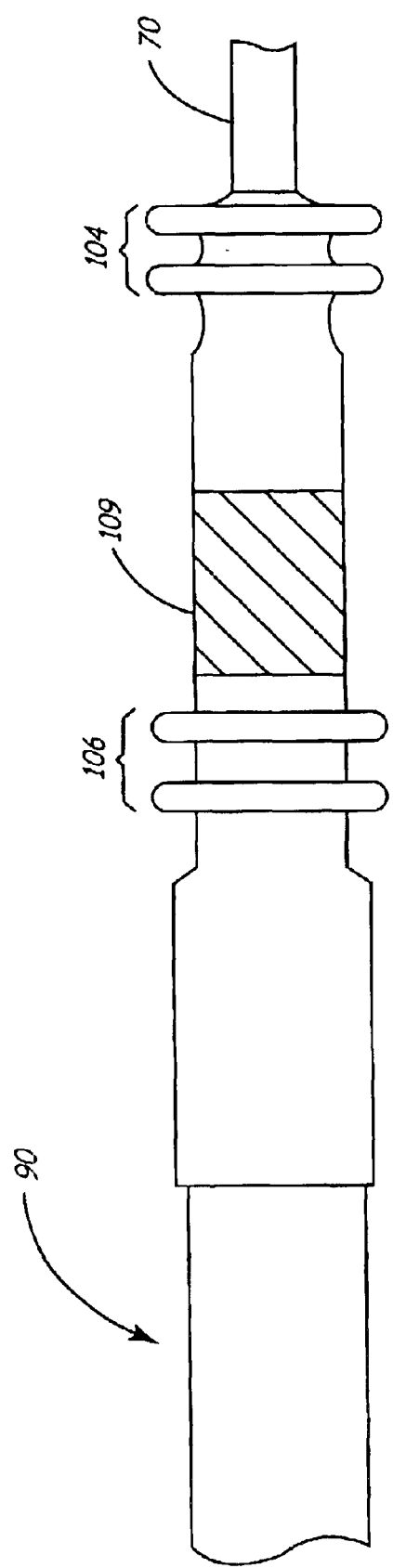
FIG. 3 is a plan view illustrating proximal end of the lead of FIG. 1C inserted within upsizing sleeve.

FIG. 3 is a plan view illustrating proximal end 90 of the lead of FIG. 1C inserted within upsizing sleeve 100. Connector pin 70 extends through the proximal end of the upsizing sleeve, whereas the lead body of proximal end extends out the distal end of the upsizing sleeve.

Figure 4A:
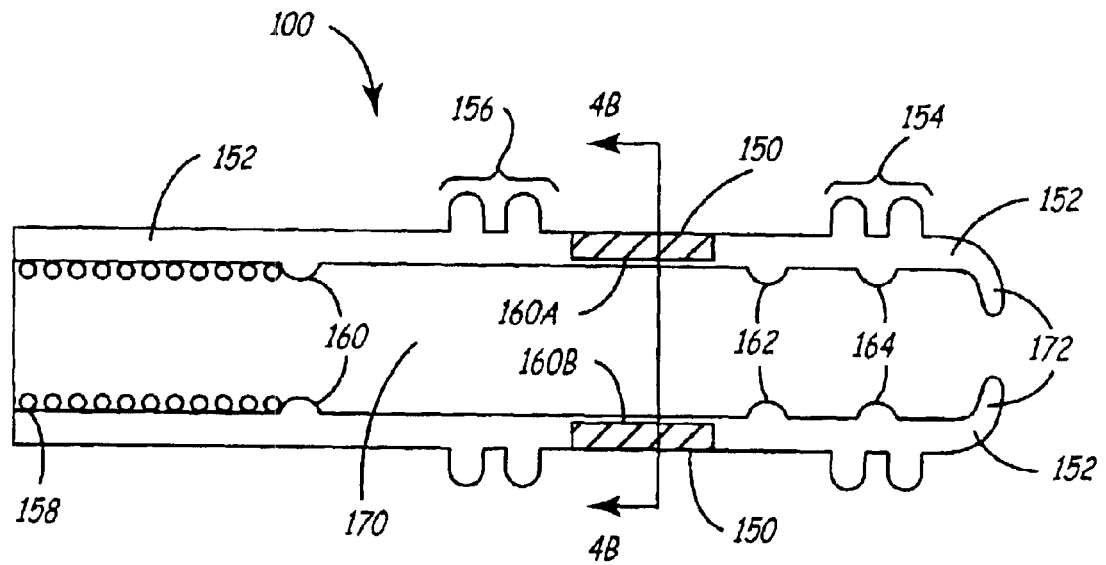
FIG. 4A is a side cutaway view of one embodiment of the upsizing sleeve of the current invention that may be formed using an over-molding process.

FIG. 4A is a side cutaway view of one embodiment of upsizing sleeve 100. A conductive ring member 150 is provided to couple to a connector ring such as connector ring 73 (FIG. 1C) of a lead in the manner discussed above. This ring member may be formed of any conductive material such as a stainless steel, for example. The remainder of the upsizing sleeve is an integral structure 152 that includes sealing rings 154 and 156. This structure may be formed of a biocompatible polymer such as silicone using a silicone over-molding process as is known in the art. According to one aspect of the invention, the upsizing sleeve may be reinforced at the distal end with a reinforcing member 158 that may be formed of an insulative coil such as a PTFE coil, a conductor coil that may or may not be insulated, or any other material having strength properties that make it suitable for this purpose. This reinforcing member provides added support to prevent the lead proximal end 90 (FIG. 3) from flexing in a manner that may cause lead failures over time. In another embodiment, a reinforcing, tubular sleeve member may be inserted within the distal end of the upsizing sleeve to provide this type of support.

Upsizing sleeve may further include interior sealing rings within the inner lumen 170. For example, upsizing sleeve of FIG. 4A includes sealing rings 160, 162 and 164 to provide a fluid-tight seal with a lead inserted within inner lumen 170. Finally, upsizing sleeve is also show to have a lip 172 at the proximal end which may be provided to engage a corresponding structure on the lead. In this manner, upsizing sleeve is positioned over the lead so that connector pin 70 extends beyond the proximal end of upsizing sleeve 100 a predetermined distance that conforms to a given connector standard. For example, lip 172 may be adapted to engage the ridge formed by insulative sleeve 75 where the insulative sleeve meets the connector 70 (FIG. 1C).

Figure 4B:
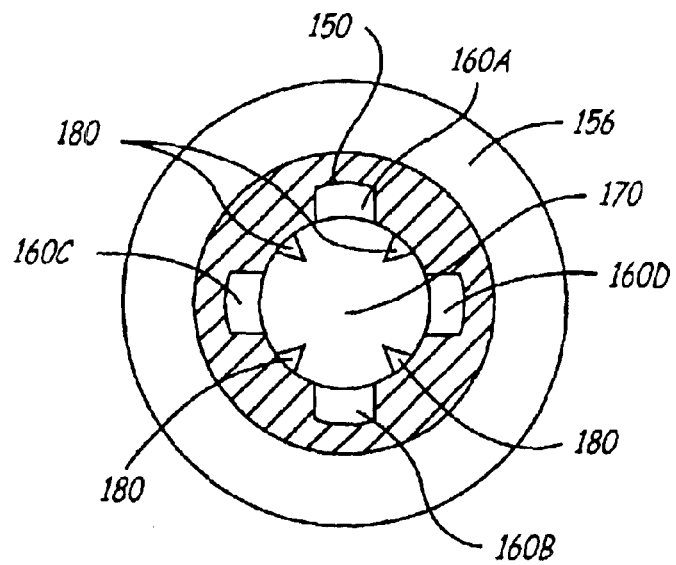
FIG. 4B is a cross-sectional view of upsizing sleeve at line 4B—4B of FIG. 4A.

FIG. 4B is a cross-sectional view of upsizing sleeve at line 4B—4B of FIG. 4A. This view shows conductive ring member 150 including channels adapted to receive a polymer during an over-molding process such as a silicon over-molding process discussed above. The flow of a polymer into these channels results in the formation of the connecting polymer structures 160A, 160B, 160C, and 160D. FIG. 4B further illustrates conductive teeth members 180 coupled to, or integrally formed, in conductive ring member 150. These conductive teeth members are adapted to engage a conductive ring of a lead such as connector ring 73 to form a more robust electrical connection between the connector ring and conductive ring member 150. This view further illustrates sealing rings 156.

Although teeth members 180 are shown in FIG. 4B to couple conductive ring member to a connector ring of a lead, many other mechanisms may be used in the alternative. For example, a keyed mechanism such as a woodruff or spline key may be used to lock a lead ring connector to the conductive ring member. Alternatively, a threaded aperture may be provided in the connective ring member so that a set-screw from a device connector block may be used to affix the sleeve to the lead via the threaded aperture. In yet another embodiment, small ports may be provided in the conductive ring member to receive conductive adhesive to enhance the electrical and mechanical contact between the conductive ring member and the lead ring connector. Alternatively, a hole in the conductive ring member may be aligned with a corresponding hole or groove in the lead so that a pin or rivet can be inserted to form a mechanical and electrical coupling. A thumb-actuated spring and ball-detent mechanism could be used to couple the sleeve to the lead. Another embodiment may include a thumb-activated push-collar such as is provided on steerable stylet handles. Any other type of coupling mechanisms may be used to form a stable electrical and mechanical fit between the conductive ring member and the connector ring of a lead.

Figure 5:
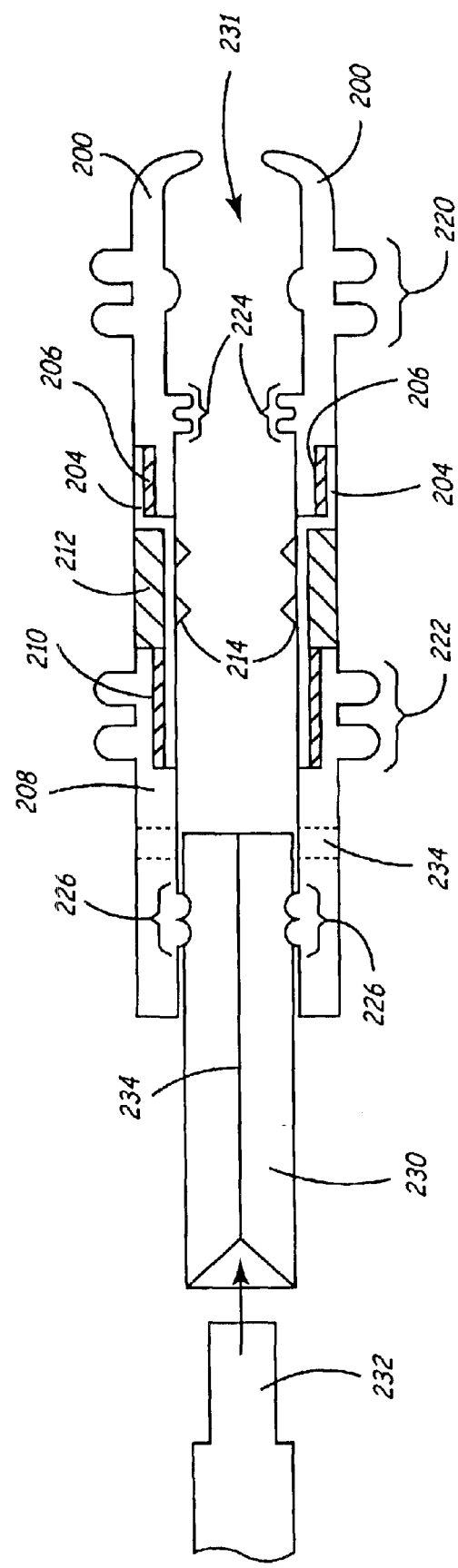
FIG. 5 is a cutaway side view of another embodiment of the upsizing sleeve of the current invention.

FIG. 5 is a cutaway side view of another embodiment of the upsizing sleeve of the current invention. In this embodiment, a first generally tubular member 200 which may be formed of silicone is bonded to a support member 204 using a first layer 206 of medical-grade adhesive. Support member, which may be formed of a material that is more rigid than the silicone such as a higher durometer polyurethane, is also bonded via adhesive layer 210 to a second generally tubular member 208, which may also be silicone. The support member 204 is adapted to provide additional structural rigidity that is not provided by a sleeve formed entirely of a lower-durometer material such as silicone. This rigidity is important to maintain precise sleeve dimensions so that the sleeve maintains a form that conforms to a predetermined standard even after undergoing the strain of forming a press fit with a lead.

A conductive ring member 212 surrounds the support member 204 and is adapted to engage a set-screw of a medical device as is provided on a standard IS-1 device connector block. In one embodiment, the conductive ring member 212 includes teeth 214 that extend through the support member to engage a connector ring of a bipolar lead. If a unipolar lead is to be employed, these teeth need not be included in the sleeve, since the ring connector of the lead need not make an electrical connection with a device connector block.

Each of tubular members 200 and 208 includes exterior sealing rings 220 and 222, respectively, to provide a fluid-tight seal with a device connector block. Each of the tubular members further includes interior sealing rings 224 and 226, respectively, to provide the fluid tight seal with a lead. As discussed above, preferably tubular members 200 and 208 are formed of a less rigid material such as silicone so that these sealing rings are more deformable and better able to provide a seal.

FIG. 5 also illustrates an alternative mechanism that may be used to engage a lead with the sleeve. A split tubular member composed of a material having a lubricious surface such as PTFE tubing 230 may be inserted in the distal end of the sleeve. The lubricious outer surface of the tubing allows the tubing 230 to be readily inserted into inner lumen 231 of the sleeve. A lead 232 may then be inserted within the inner lumen of the tubing 230 and the tubing removed. The slit 234 in the tubing allows it to be removed from around the lead after the lead is attached to the up-sizing sleeve. The use of this split tubular member thereby provides an alternative to the pull-wire tool (FIG. 2) as an aid to forming the press fit between a lead and the sleeve.

In one embodiment, sleeve may include one or more ports such as port 234 (shown dashed) to allow a medical-grade adhesive to be infused or injected between the sleeve and the lead after the lead is inserted into the sleeve to thereby secure the lead to the sleeve.

Figure 6:
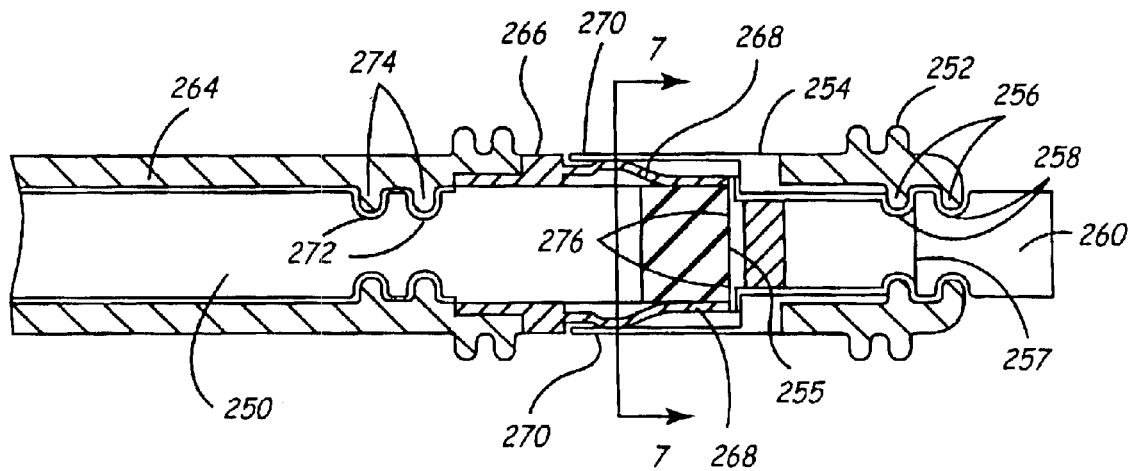
FIG. 6 is a cutaway side view of a two-piece sleeve member that may be assembled over the lead at the time of use.

FIG. 6 is a cutaway side view of a two-piece sleeve member that may be assembled over a lead such as lead 250 at the time of use. A first portion of the sleeve includes a less rigid, generally tubular member 252 that may be formed of silicon, and which is bonded to a conductive ring 254 via a medical-grade adhesive. Conductive ring 254, which is formed of a conductive material, is adapted to electrically and mechanically couple to a connector ring 255 of lead 250 via a second portion of the sleeve, as will be discussed further below. Conductive ring is further adapted to electrically couple to a connector block of a medical device, as may be accomplished using a set-screw.

In one embodiment, the tubular member 252 includes one or more lips 256 to engage grooved members 258 in the lead connector pin 260. This allows the sleeve to be seated over the lead so that the dimensions of the assembly conform to a predetermined standard such as IS-1. Lips 256 further provides a fluid-tight seal with lead 250. One of the lips 256 is shown interfacing with a seal zone 257 of the inline connector. As discussed above, tubular member 252 may be formed of a less rigid material such as silicone to provide sealing rings that allow for a better fluid-tight seal.

The two-piece sleeve of FIG. 6 further includes a second portion that is formed of a second less-rigid tubular member 264 such as silicone. Tubular member 264 is bonded to a connector member 266, which may be formed of a metal. Connector member 266 has deformable fingers 268 that slide under edge 270 to engage conductive ring 254 in a snap-fit that provides both a mechanical and electrical coupling between connector member 266 and conductive ring 254. Deformable fingers 268 also electrically couple to connector ring 255 of lead 250 so that an electrical connection is formed between the connector ring 255 and conductive ring 254 of the two-piece sleeve. This allows the connector ring 255 of lead 250 to be coupled to a connector block of a device via conductive ring 254.

The lead 250 of FIG. 6 may include grooves 272 to engage inner sealing rings 274, and may further having a shoulder 276 to engage conductive ring 254 in a manner that further allows the lead to seat in a position that conforms to a predetermined standard.

Figure 7:
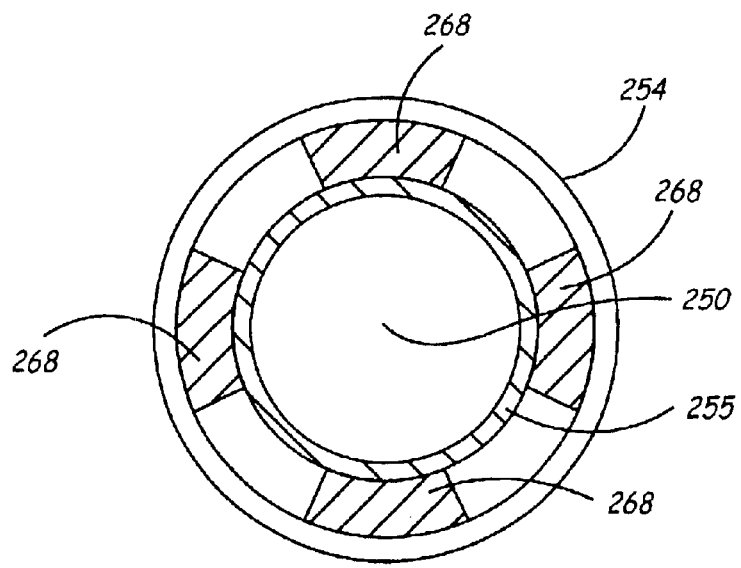
FIG. 7 is a cross-sectional view of the sleeve of FIG. 6 at line 7—7.

FIG. 7 is a cross-sectional view of the sleeve of FIG. 6 at line 7—7. This view shows the deformable fingers 268 electrically and mechanically engaging conductive ring 254, and further electrically engaging connector ring 255 of lead 250.

Figure 8:
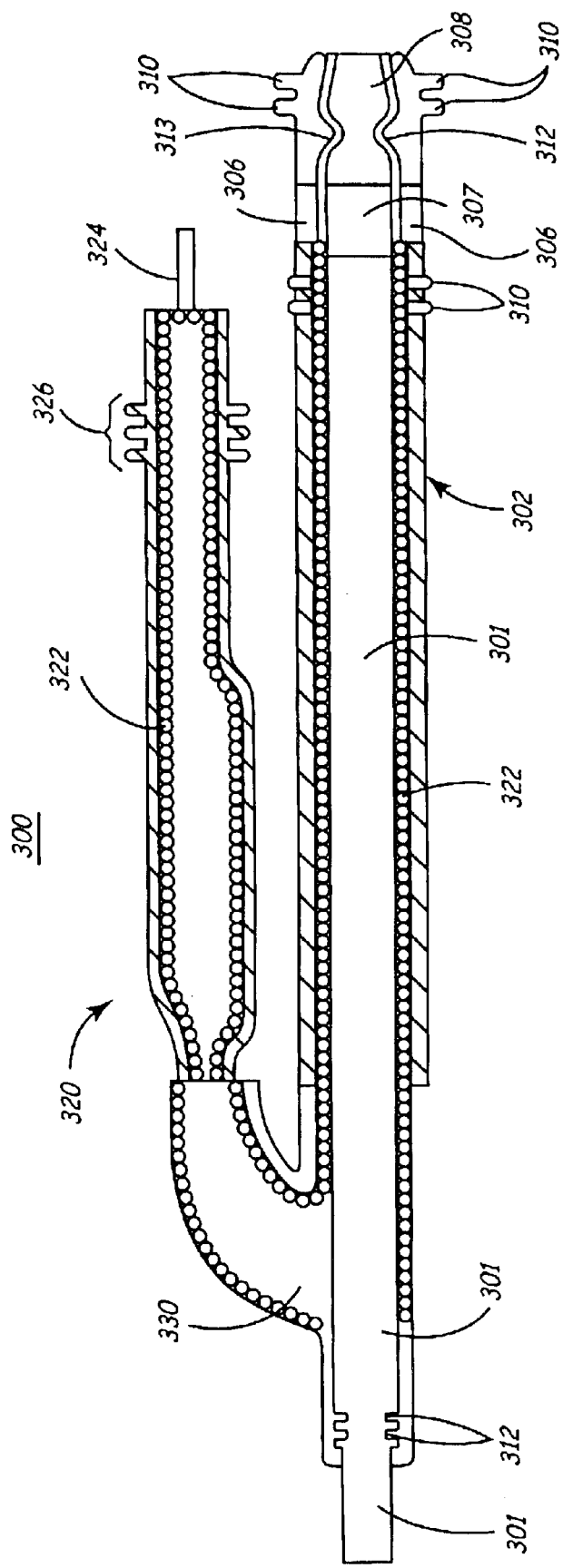
FIG. 8 is a cutaway side view of a bifurcated sleeve that includes two different connector standards.

FIG. 8 is a cutaway side view of a bifurcated sleeve 300 designed to adapt a lead to conform to two different connector standards. In the embodiment illustrated, lead 301 is shown engaging a first bifurcation leg 302 of the bifurcated sleeve that conforms to the IS-1 standard. This portion of the sleeve may be of any of the embodiments discussed above. A conductive ring member 306 is provided on bifurcation 302 to engage with a connector ring 307 of lead 301, and to further engage a connector block of a medical device in the manner discussed above. The pin 308 of the lead extends through the sleeve as discussed above, and exterior sealing rings 310 provide a fluid-tight fit with the medical device. Interior sealing rings 312 and 313 provide a fluid-tight fit with lead 301. Additional inner sealing rings (not shown) are provided to engage the proximal end of the lead as discussed above.

In this embodiment, pacing and sensing of a patient may be accomplished via ring connector 306 and pin 308 connectors, which coupled to tip and ring electrodes (not shown in FIG. 8), respectively, at the lead tip. Further assume the lead carries a high-voltage coil electrode that is electrically coupled to ring connector 306. An offset bifurcation leg 320 may then be used to provide a connector for cardioversion/defibrillation purposes. A high-voltage defibrillation coil 322 connects conductive ring member 306 with a connector pin 324 that may conform to a second standard such as a DF-1 standard. This connector pin 324 may be utilized by a medical device to deliver a cardioversion/defibrillation shock that is then carried via coil 322 and conductive ring member 306 to conductor ring 307, and finally to the defibrillation coil electrode as the proximal end of the lead. This embodiment of the sleeve thereby allows a bipolar lead having a pace/sense electrode pair and a single shock coil to be adapted to both IS-1 and DF-1 connector blocks without the need to slit or split a catheter that is used during lead delivery. Additionally, the current inventive sleeve eliminates the pocket bulk associated with traditional longitudinal adaptors.

Sleeve 300 may be formed of one or more biocompatible polymers. For example, the hub portion 330 of the bifurcated sleeve could be formed of a more rigid material such as polyurethane that provides additional support to the structure and to the proximal end of the lead. The remainder of the sleeve, including the portions of the legs 302 and 320 that include the exterior sealing rings 310 and 326, could be formed of a less rigid material such as silicone.

As noted above, the current inventive up-sizing sleeve is, in its preferred embodiment, designed to conform a lead to a predetermined connector standard. For this reason, it is important that the sleeve does not stretch or deform in any manner. To provide a structure that maintains precise dimensions, more rigid support structures formed of a material such as polyurethane may be incorporated into the sleeve. The inclusion of additional sealing grommets may also be desirable to ensure both a fluid-tight seal, and the retention of predetermined sleeve dimensions.

Figure 9:
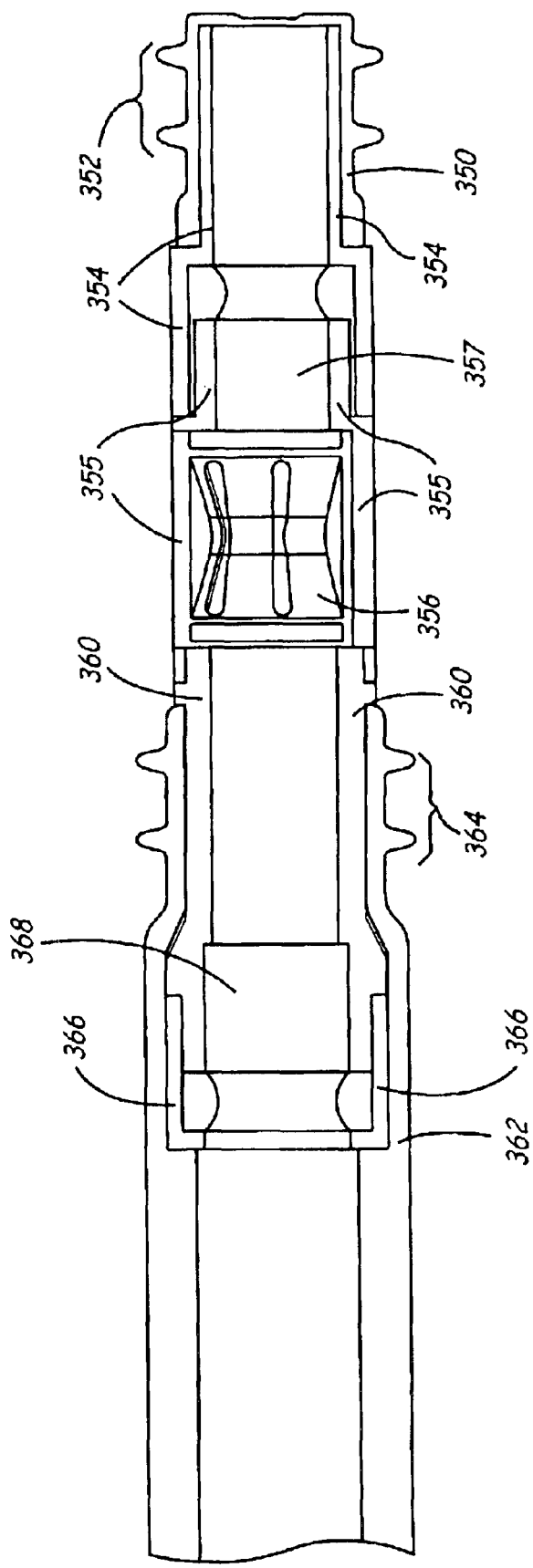
FIG. 9 is a side cutaway view of another embodiment of the current invention that incorporates both support structures and sealing grommets.

FIG. 9 is a side cutaway view of another embodiment of the current inventive up-sizing sleeve that incorporates both support structures and sealing grommets. A first, less-rigid tubular sleeve member 350 is shown having exterior sealing rings 352 as discussed above. Tubular member 350, which may be formed of a silicone, is bonded to a more rigid tubular support member 354, which may be formed of a polyurethane. Support member 354, is, in turn, coupled at one end to an exterior conductive ring 355 formed of an electrically-conductive material that is adapted to make an electrical connection with a connector block of a medical device, as is provided by a standard IS-1 connector.

Conductive ring 355 houses, and is mechanically and electrically coupled to, a connector member 356 that is also formed of a conductive material. Connector member 356 is adapted to make an electrical and mechanical connection with a connector ring of a lead in a manner similar to that discussed above. Connector member 356 is shown in this embodiment to be a multi-beam connector having deformable fingers adapted to form a press-fit with a lead connector ring. Alternatively, connector member 356 may take the form of any other type of connector known in the art, including any of the types of connectors discussed above.

Housed within conductive ring 354 may be a sealing grommet 357 provided to form a superior fluid-tight seal with a lead. Sealing grommet 357 may be formed of a more deformable material such a silicone, for example.

Conductive ring 355 is further bonded or welded to a second rigid tubular support member 360, which may be formed of a polyurethane or a metal. This second tubular support member 360 is also mechanically coupled to a less rigid, tubular sleeve member 362 having sealing rings 364, and which may be formed of silicone. Tubular support member 360 is bonded to a lip member 366 adapted to house a second sealing grommet 368. Lip member 366 may be formed of a rigid polymer such as a polyurethane, whereas the sealing grommet may be formed of silicone.

The embodiment shown in FIG. 9 provides a more flexible design. The length of the sealing grommets may be adjusted to position the conductive ring 355 based on a selected connector standard. Moreover, the multi-beam connector shown as connector member 356 may be adjusted to couple to any lead size requirement. This design is adaptable for over-the-wire leads, and small coil-over-cable leads having an outer diameter of 5 French or less.

It may be noted that while the multi-beam connector 356 of FIG. 9 may be adapted to form an electrical connection with a connector ring of a multi-polar lead, this need not be the case. In one embodiment, the multi-beam connector 356 may be formed of a non-conductive material. In this case, the connector 356 is adapted to form a mechanical connection with a unipolar lead so that the lead body is maintained in a stable position with respect to the up-sizing sleeve. In this embodiment, conductive ring 355 may be omitted if desired, or a similar structure may be provided that is formed of a non-conductive material.

Figure 10A:
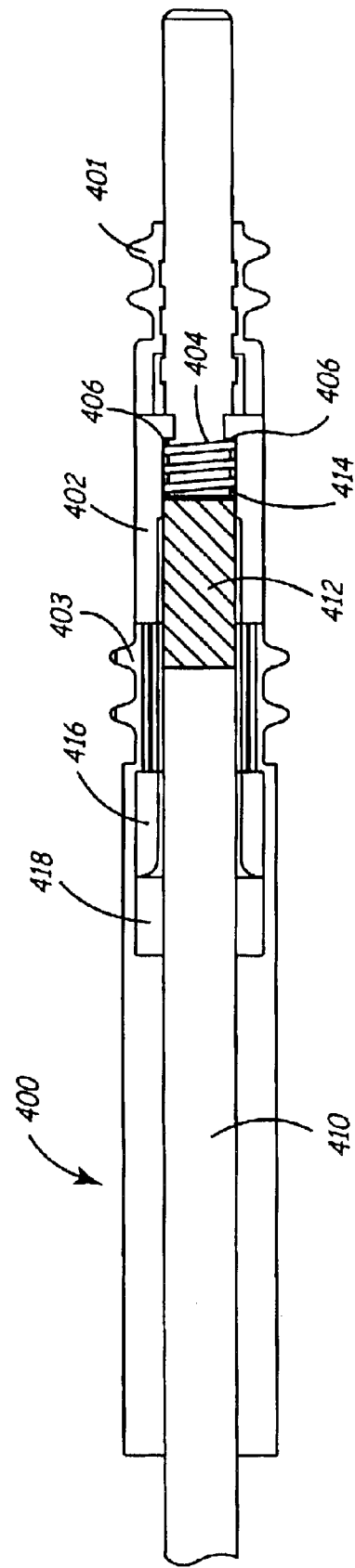
FIG. 10A is a side cutaway view showing an embodiment of the up-sizing sleeve that includes a spring coil to form the electrical connection between a lead ring connector and a conductive ring member of the upsizing sleeve.

FIG. 10A is a side cutaway view showing yet another embodiment of the up-sizing sleeve that includes a spring coil to form the electrical connection between a lead ring connector and a conductive ring member of the upsizing sleeve 400. Up-sizing sleeve 400 includes many of the components described above with respect to other ones of the embodiments of the invention. For example, the embodiment of FIG. 10A includes flexible tubular members 401 and 403 which may be formed of a silicone, and which are coupled as with a medical-grade adhesive to an electrically-conductive ring member 402. Most notably, in this embodiment, conductive ring member 402 is electrically and mechanically coupled at one end to a deformable spring coil 404. Spring coil 404, which is formed of an electrically-conductive material, may be spot welded or otherwise coupled to a shoulder 406 of conductive ring member 402. In this embodiment, lead 410 includes a ring conductor 412 having a lip 414 to engage spring coil 404. In this manner, ring connector 412 is electrically coupled to the conductive ring member 402, which, in turn, may be coupled to the connector block of a medical device. The upsizing sleeve may further include one or more grommets such as grommet 416, which is maintained in position by a polyurethane lip member 418 similar to that shown in the embodiment of FIG. 9. The upsizing sleeve may further include other aspects described with respect to the embodiments of FIGS. 1–9 as would be apparent to those skilled in the art.

Figure 10B:
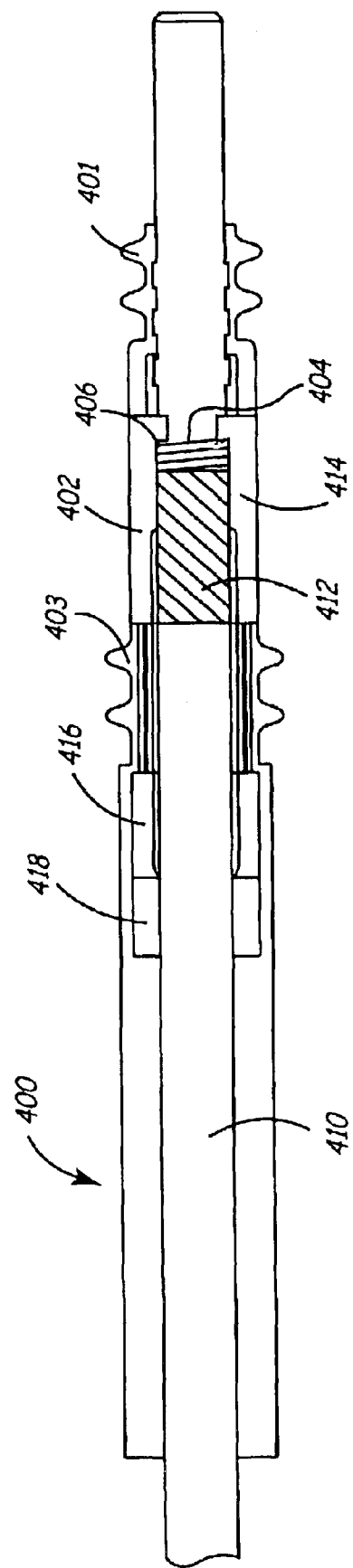
FIG. 10B is a side cutaway view of the embodiment of FIG. 10A illustrating the manner in which the spring coil compresses when the lead is fully inserted within the up-sizing sleeve.

FIG. 10B is a side cutaway view of the embodiment of FIG. 10A illustrating the manner in which the spring coil 404 compresses when the lead is fully inserted within the up-sizing sleeve 400.

Figure 11:
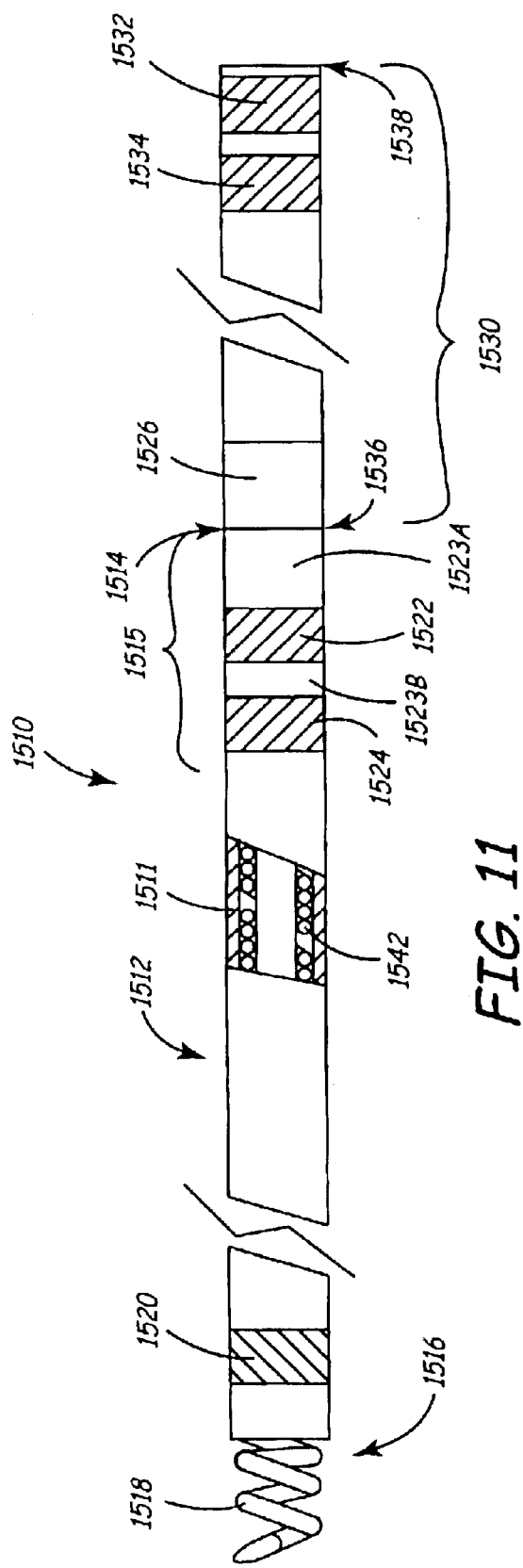
FIG. 11 is a plan view, with a partial section, of a lead according to one embodiment of the present invention.

FIG. 11 is a plan view of a lead 1510 according to one embodiment of the present invention. Lead 1510 includes an elongated lead body 1512 and an elongated extension 1530. As illustrated in FIG. 11, lead body 1512, extending between a proximal end 1514 and a distal end 1516, includes an outer insulation 1511, a conductor coil 1542, tip electrode 1518, ring electrode 1520, and a proximal portion 1515 including connector rings 1522 and 1524, a first insulative spacer 1523A and second insulative spacer 1523B. The outer insulation 1511 may be formed from a resilient biocompatible plastic, such as silicone rubber or polyurethane, and the conductor coil 1542 may include MP35N alloy wires or wires made from any other biocompatible and biostable materials that are capable of reliably conducting electrical current after having been subjected to repeated bending and torsion loads.

Lead 1510 is shown as a bipolar lead in FIG. 11 having two connector rings 1524 and 1522, separated by second insulative spacer 1523B and joined via filars of conductor coil 1542 (shown in more detail in FIG. 12A) to tip electrode 1518 and ring electrode 1520 at the distal lead end 1516. In other embodiments, lead 1510 may be a unipolar, bipolar or multipolar lead, for pacing, sensing, and/or defibrillation, having multiple connector rings joined to any of a tip electrode, one or more ring electrodes, or one or more coil electrodes, or other types of sensors carried by lead body 1512.

As illustrated in FIG. 11, extension 1530 has a distal end 1536 attached to proximal end 1514 of lead 1510 and extends to a proximal end 1538. Extension 1530, being generally tubular, carries temporary contact surfaces 1532 and 1534, in proximity to its proximal end 1538, which are joined to corresponding connector rings 1522 and 1524 via conductors, various embodiments of which conductors are described in conjunction with FIGS. 12A–D. As illustrated in FIG. 11, extension 1530 includes a severing section 1526 in proximity to distal end 1536, which is separated from connector ring 1522 by first insulative spacer 1523A. According to one embodiment of the present invention, severing section 1526 may be marked to distinguish it from a remainder of extension 1530; for example, severing section 526 may be transparent while the remainder of extension 1530 is opaque, or severing section may include a color that distinguishes it from the remainder of extension 1530, or severing section 1526 may have a physical deformation such as a narrow groove on an outer diameter. Extension 1530 further includes a member having a relatively low extensibility, various embodiments of which will be described in conjunction with FIGS. 12A–D. Extension 1530 has a length corresponding to a length of a guide catheter, as will be described in more detail below in conjunction with FIG. 17, and, in one embodiment, according to the present invention, extension 1530 has a maximum outer diameter less than or equal to a minimum outer diameter of lead 1510.

Figure 12A:
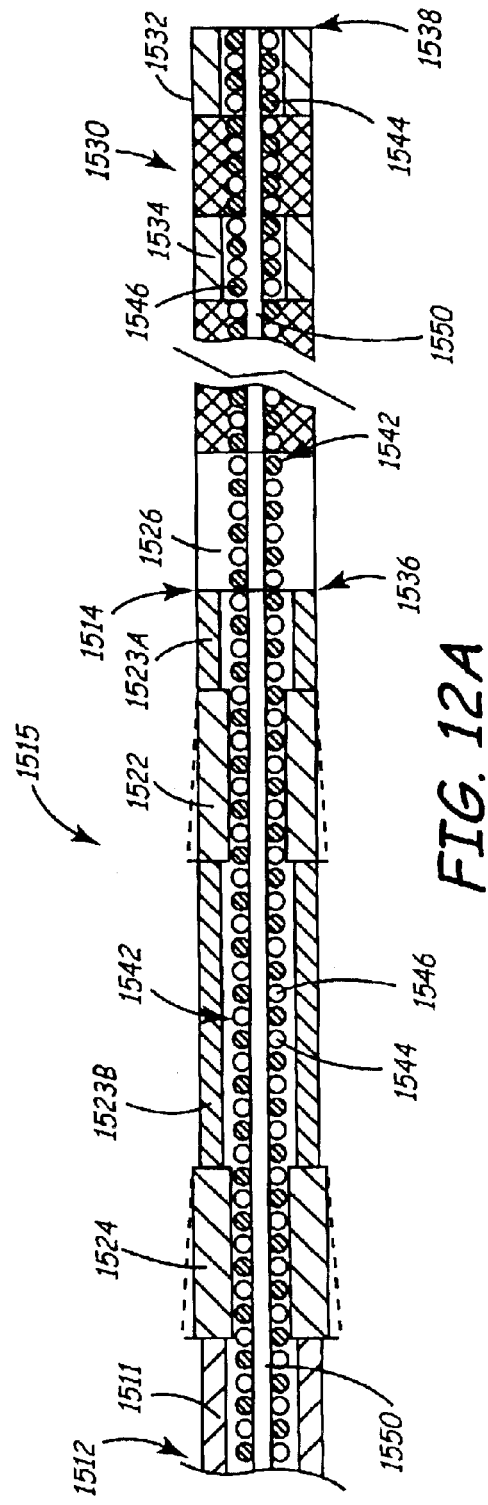
FIG. 12A is an exploded, side, cut-away view of one embodiment of the proximal portion and extension of the lead shown in FIG. 11.

FIG. 12A is an exploded, side, cut-away view of one embodiment of proximal portion 1515 and extension 1530 of lead 1510. As illustrated in FIG. 12A, connector rings 1522 and 1524 are approximately isodiametric with lead body 1512, however, connector ring 1524 may have a slightly greater outer diameter than connector ring 1522. In alternate embodiments connector rings 1522 and/or 1524 may have a tapered outer diameter as indicated by dashed lines in FIG. 12A. In further alternate embodiments according to the present invention, having more than two connector rings, outer diameters of rings step down from a largest diameter for a most distal ring, corresponding to connector ring 1524, to a smallest diameter for a most proximal ring, corresponding to connector ring 1522. Connector rings, such as rings 1522 and 1524 are formed from a biocompatible, conductive material, such as stainless steel.

FIG. 12A illustrates conductor coil 1542 including multiple filars 1544 and 1546, wherein filar 1544 is electrically coupled to connector ring 1522 and filar 1546 is electrically coupled to connector ring 1524 by welding, crimping or other means well known to those skilled in the art of lead construction. Filars 1544 and 1546 are further coupled to electrodes, such as tip electrode 1518 and ring electrode 1520 (shown in FIG. 11), by welding, crimping or other means well known to those skilled in the art. According to one embodiment of the present invention, filars 1544 and 1546 are electrically insulated from one another by means of an insulative coating about one or both of the filars; the insulative coating may be composed of a durable, biocompatible and biostable polymer, such as ETFE or polyamide. As illustrated in FIG. 12A, conductor coil 1542 extends from proximal portion 1515 of lead 1510 into extension 1530 where filar 1544 is electrically coupled to contact surface 1532 and filar 1546 is electrically coupled to contact surface 1534. In this manner, contact surfaces 1532 and 1534, in addition to connector rings 1522 and 1524, are electrically coupled via filars 1544 and 1546 of conductor coil 1542 to electrodes, such as tip electrode 1518 and ring electrode 1520, respectively, shown in FIG. 11.

FIG. 12A further illustrates an elongate member 1550, having a relatively low extensibility (i.e. being relatively non-compliant) and relatively high tensile strength, extending through a lumen of conductor coil 1542, from proximal end 1538 of extension 1530 and into lead body 1512. According to one embodiment of the present invention member 550 extends to electrode tip 1518 (shown in FIG. 11) and is formed from polyester fiber providing tensile strength to lead 1510 and extension 1530. Such an embodiment of member 1550 is described in International PCT Publication No. WO 01/80941 issued to Williams, et al., incorporated herein by reference in its entirety. In an alternate embodiment according to the present invention, member 1550 may be absent wherein an outer tubing, formed of a biocompatible insulative material, may provide relatively high tensile strength and relatively low extensibility to lead body 1512 and extension 1530 or to just extension 1530.

Figure 12B:
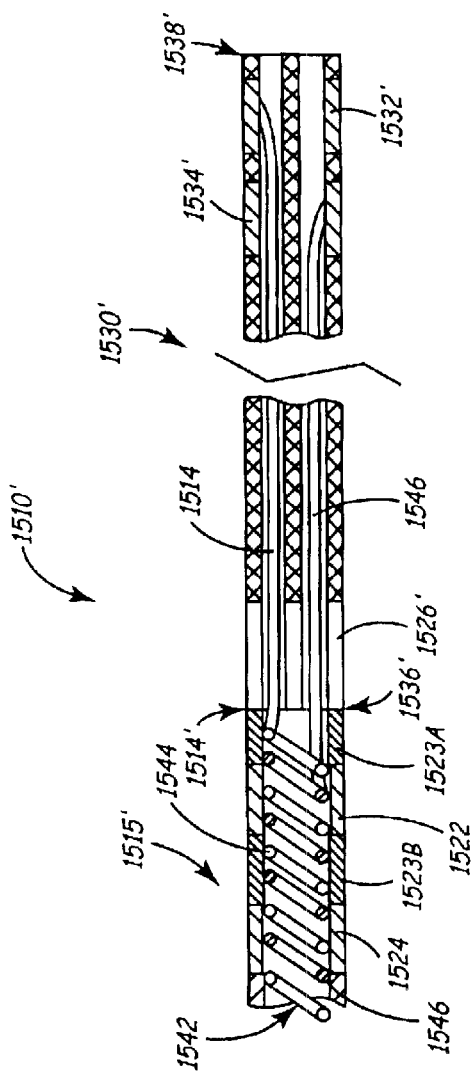
FIG. 12B is an exploded, side, cut-away view of a second embodiment of the proximal portion and extension of the lead shown in FIG. 11.

FIG. 12B is an exploded, side, cut-away view of a second embodiment of a proximal portion 1515' and an extension 1530' of a lead 1510'. As illustrated in FIG. 12B, filars 1544 and 1546 of conductor coil 1542 are unwound in proximity to proximal end 1514' of proximal portion 1515' in order to be routed into a distal end 1536' of extension 1530' having a bi-lumen form. As in the embodiment depicted in FIG. 12A, filars 1544 and 1546 are electrically coupled to connector rings 1522 and 1524 and to contact surfaces 1532' and 1534' and a severing section 1526' is positioned in proximity to distal end 1536' and may be marked in a similar manner described above in conjunction with FIG. 11.

Figure 12C:
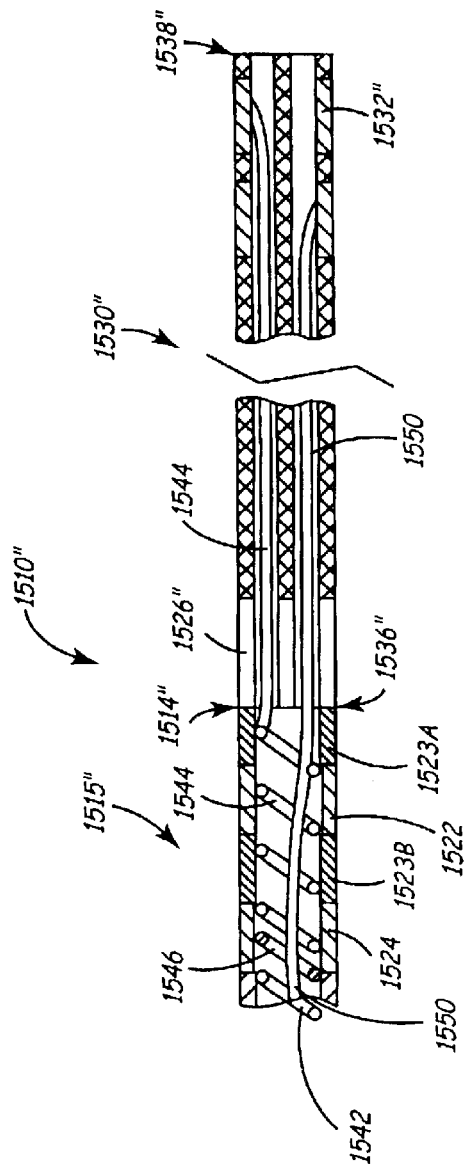
FIG. 12C is an exploded, side, cut-away view of a third embodiment of the proximal portion and extension of the lead shown in FIG. 11.

FIG. 12C is an exploded, side, cut-away view of a third embodiment of a proximal portion 1515" and an extension 1530", having a bi-lumen form similar to that depicted in FIG. 12B, of a lead 1510". As illustrated in FIG. 12C, filar 1544 is routed into a first lumen of extension 1530" and is electrically coupled to both connector ring 1522 and a single contact surface 1532" of extension 1530" while filar 1546 is only electrically coupled to connector ring 1524 and is not extended into extension 1530". In one embodiment according to the present invention, filar 1544 joins connector ring 1522 and contact surface 1532" to a tip electrode, for example tip electrode 1518 shown in FIG. 11. FIG. 12C further illustrates member 1550 extending from proximal portion 1515" into one of the lumens of extension 1530" to provide tensile strength and to limit extensibility. It should be noted that a similar alternate embodiment of proximal portion 1515 and extension 1530 depicted in FIG. 12A may be formed by terminating filar 1546 within proximal end 1515 and eliminating contact surface 1534 of extension 1530.

Figure 12D:
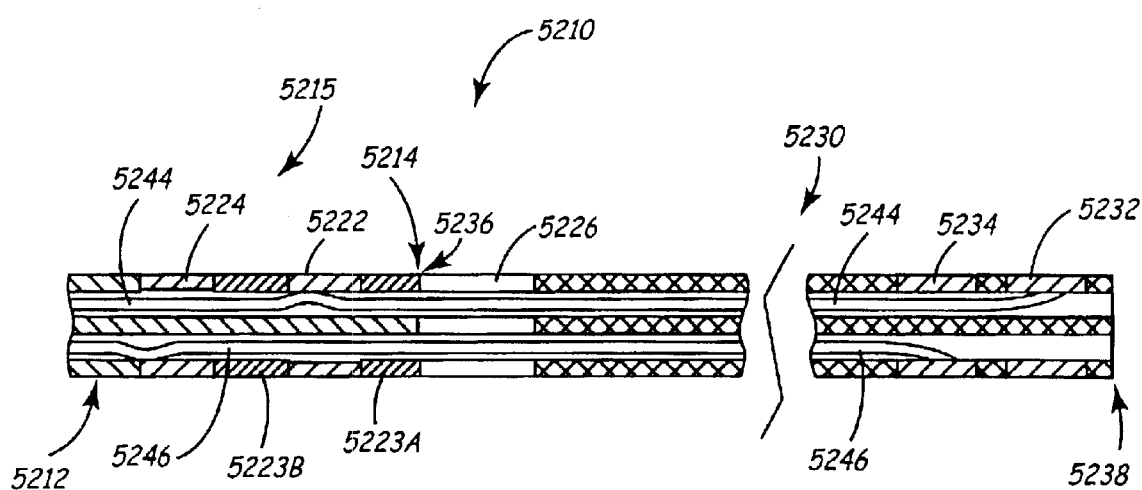
FIG. 12D is an exploded, side, cut-away view of a proximal portion and an extension of a lead according to an alternate embodiment of the present invention.

FIG. 12D is an exploded, side, cut-away view of a lead 5210 including a lead body 5212, having a proximal portion 5215, and an extension 5230, joined at a proximal end 5214, having a severing section 5226, in proximity to a distal end 5236, and contact surfaces 5232 and 5234 in proximity to a proximal end 5238. As illustrated in FIG. 12D both lead body 5212 and extension 5230 are in a bi-lumen form and conductors 5244 and 5246 are cable-type conductors, many forms of which are well known to those skilled in the art of lead construction. Conductor 5244 is electrically coupled to connector ring 5222 and conductor 5246 is electrically coupled to connector ring 5224 by welding, crimping or other means well known to those skilled in the art. Conductors 5244 and 5246 are further coupled to electrodes, such as tip electrode 1518 and ring electrode 1520 (shown in FIG. 11), by welding, crimping or other means well known to those skilled in the art. FIG. 12D further illustrates conductors 5244 and 5246 extending from proximal portion 5215 of lead 5210 into extension 5230 where conductor 5244 is electrically coupled to contact surface 5232 and conductor 5246 is electrically coupled to contact surface 5234. In this manner, contact surfaces 5232 and 5234, in addition to connector rings 5222 and 5224, are electrically coupled via conductors 5244 and 5246 to electrodes such as tip electrode 18 and ring electrode 1520, respectively, shown in FIG. 11. Furthermore conductors 5244 and 5246 in a cable form provide relatively high tensile strength and relatively low extensibility for lead body 5212 and extension 5230.

Although conductors have been illustrated in the forgoing as being continuous from a lead body to an extension, according to alternate embodiments of the present invention, separate conductors may be employed for a lead body and an extension; for example, filar 1544 in FIG. 12B may be terminated in a coupling with connector ring 1522 and a separate wire or cable-like conductor may also be coupled to connector ring 1522 and extended into extension 1530' for coupling with contact surface 1532'.

FIG. 13 is a plan view of a connector sleeve assembly 5100 to be used in conjunction with a lead, such as lead 1510, 1510', 1510", or 5210, according to one embodiment of the present invention. Sleeve assembly 5100 includes a generally tubular sleeve body 5106 having a distal end 5105 and a proximal end 6103 and a central lumen (not shown in FIG. 13). Sleeve body 5106 may formed from a resilient biocompatible plastic, such as molded silicone rubber. The outer dimensions of sleeve assembly 5100 are sized to fit a connector block port, for example an IS-1 connector port, of a medical device.

Sleeve assembly 5100 further includes a reinforcing coil 5112, outer sealing rings 6108 and 6110, a pin terminal 5102, at proximal end 6103, and a ring terminal 5104, spaced distally from pin terminal 5102. Pin terminal 5102 and ring terminal 5104 may be sized to conform to an industry connector standard, such as an IS-1 standard.

Sleeve assembly 5100 is shown in FIG. 13 to be bipolar, having one pin terminal 6103 and one ring terminal 5104. A unipolar sleeve assembly having only a pin terminal or only a ring terminal is also contemplated for use with a corresponding unipolar lead having one connector ring. Furthermore, a multipolar connector sleeve assembly is contemplated having a pin terminal and/or multiple ring terminals for use with a corresponding multipolar lead having multiple connector rings.

FIG. 14 is a, side, cut-away view of sleeve assembly 5100 wherein sleeve assembly further includes a central lumen 5118, sized to engage a proximal portion of a lead, for example proximal portion 1515 shown in FIG. 12A, inner sealing rings 5122 and 5124, a pin connector member 5120 at proximal end 6103, and a ring connector member 5130 spaced distally from pin connector member 5120. As illustrated in FIG. 14, pin connector member 5120 includes pin terminal 5102, a spring contact 5114, and an axial through bore 5107 continuous with central lumen 5118 of sleeve body 5106 and having a proximal opening 5109. Likewise, ring connector member 5130 includes ring terminal 5104, a spring contact 5116, and an axial through bore 5111 continuous with central lumen 5118 of sleeve body 5106. Spring contacts 5114 and 5116 are shown in FIG. 14 as multi-beam contacts; however, spring contacts 5114 and 5116 may also take the form of garter or coil spring contacts, or any other type of contacts capable of providing electrical coupling as well as mechanical retention of a lead connector ring.

Figure 15A:
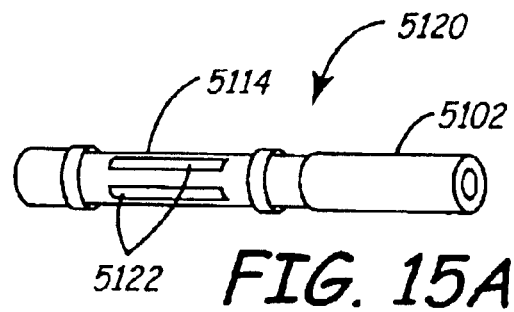
FIG. 15A is a perspective view of a pin connector member included in the connector sleeve assembly of FIG. 13.
Figure 15B:
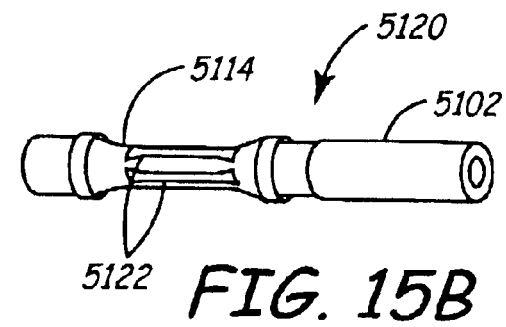
FIG. 15B is a perspective view of the pin connector member of FIG. 15A after it has been crimped to form a multi-beam contact.

FIG. 15A is a perspective view of pin connector member 5120. According to one embodiment of the present invention, pin connector member 5120 is formed by machining an electrically conductive, biocompatible material, such as stainless steel. During the machining process, material is displaced to form openings 5122 in contact 5114 to form a multi-beam contact. Contact 5114 is then crimped down as shown in the perspective view of FIG. 15B. The resulting inner diameter of contact 5114 is preferably sized to fixedly engage with a connector ring, such as connector ring 1522 of lead 1510 shown in FIG. 11 and FIG. 12A, to provide electrical contact and mechanical retention of connector ring 1522.

Figure 16A:
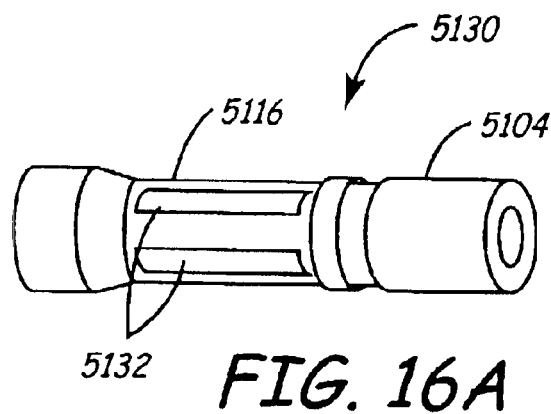
FIG. 16A is a perspective view of a ring connector member included in the connector sleeve assembly of FIG. 13.
Figure 16B:
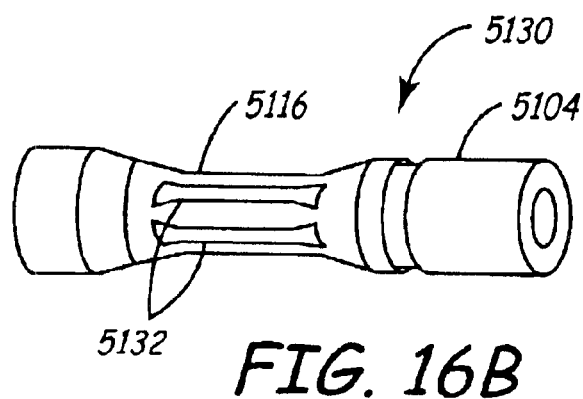
FIG. 16B is a perspective view of the ring connector member of FIG. 16A after it has been crimped to form a multi-beam contact.

FIG. 16A is a perspective view of ring connector member 5130. According to one embodiment of the present invention, ring connector member 5130 is preferably formed by machining an electrically conductive biocompatible material such as stainless steel. During the machining process, material is displaced to form openings 5132 in contact 5116 to form a multi-beam contact. Contact 5116 is then crimped down as shown in the perspective view of FIG. 16B. The resulting inner diameter of contact 5116 is preferably sized to fixedly engage with a connector ring, such as 1524 of lead 1510 shown in FIG. 11 and FIG. 12A, to provide electrical coupling and mechanical retention of connector ring 1524.

The inner diameter of contact 5116 may be slightly greater, for example on the order of between approximately 0.01 and approximately 0.04 inches, than the inner diameter of contact 5114. According to one embodiment of the present invention, this size difference corresponds to a slight size difference between connector rings 1522 and 1524 noted above in conjunction with FIG. 12A. This size difference allows more proximal connector ring 1522 to easily pass through contact 5116 as lead 1510 is pulled into connector sleeve assembly 5100. When proximal portion 1515 is fully inserted into sleeve assembly 5100, proximal connector ring 1522 will fixedly engage with contact 5114, and distal connector ring 1524 will simultaneously become fixedly engaged with contact 5116.

If lead 1510 is provided as a multi-polar lead, in one embodiment, the outer diameter of each of multiple connector rings would step up in size moving from the most proximal connector ring to the most distal connector ring. Specifically, the most proximal connector ring would be smaller than the next most proximal ring, which would be smaller than the next most proximal ring and so on. The diameter of the largest, most distal connector ring, however, would not be significantly greater than the outer diameter of the lead body, allowing a guide catheter to easily pass over the connector rings. This stepped size difference between connector rings, in one embodiment according to the present invention, allows each connector ring be pulled into a corresponding, appropriately sized contact when the lead is pulled into a multi-polar connector sleeve assembly. The multi-polar connector sleeve assembly is accordingly provided with multiple contacts having inner diameters, which step up in size moving from the most proximal contact to the most distal contact. A more proximal lead connector ring will therefore easily pass through larger, more distal, contacts of the connector sleeve until reaching the contact that is sized to fit that particular connector ring. Connector rings may simultaneously become engaged with corresponding connectors, or, alternatively, connector rings may successively engage with appropriately spaced contacts in a manner similar to that disclosed in U.S. Pat. No. 5,766,042 to Ries, et al., incorporated herein by reference in its entirety.

Figure 17:
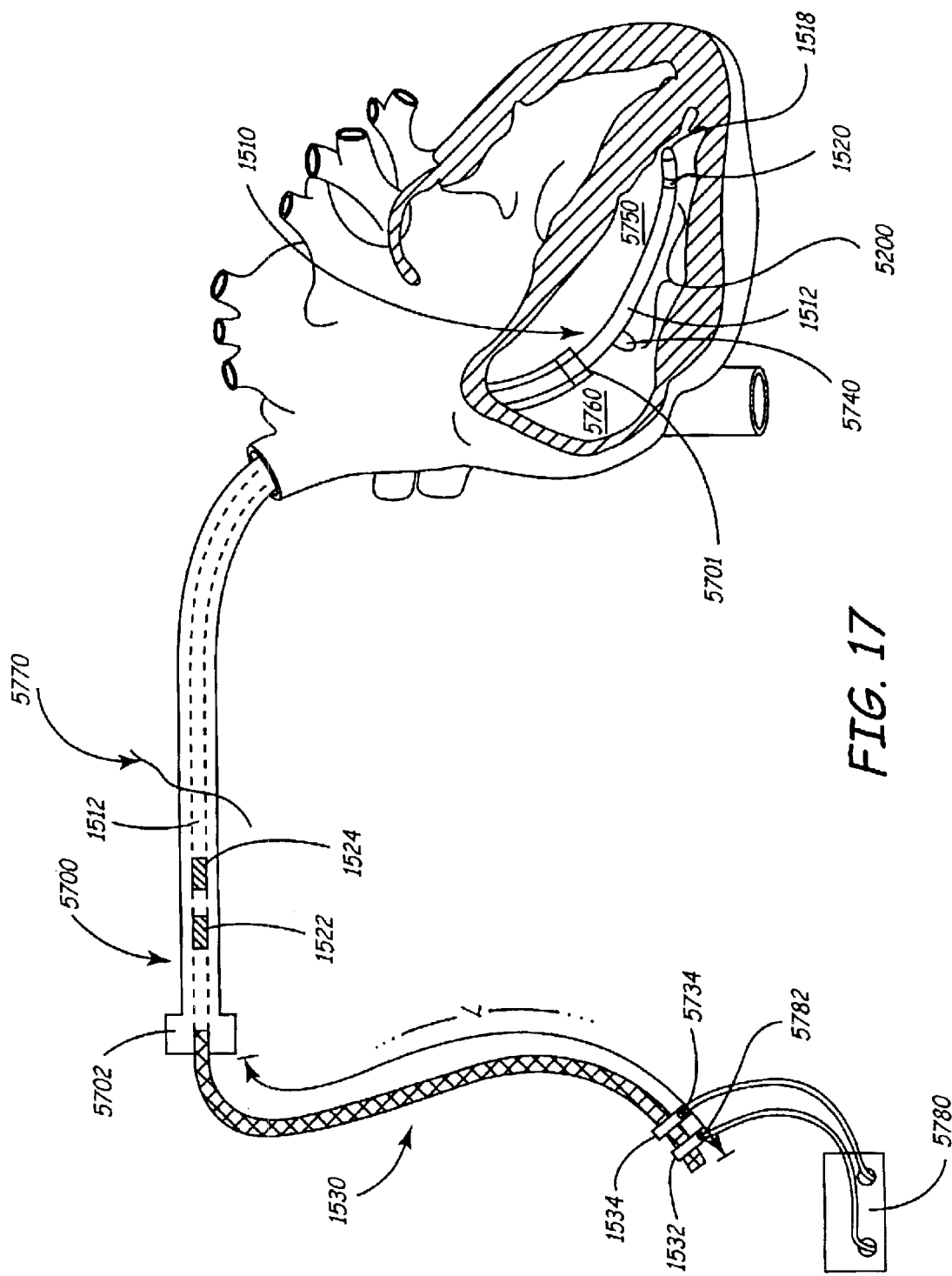
FIG. 17 is a schematic of the lead of FIG. 11 implanted via a catheter.

FIG. 17 is a schematic of lead 1510 implanted in a right ventricle 5750 of a heart via a guide catheter 5700. As illustrated in FIG. 17, guide catheter 5700 and lead 1510 have been inserted into a heart via a venous access point 5770 and tip electrode 1518 has been fixed in a wall of right ventricle 5750. Guide catheter 5700 having directed tip electrode 1518 to a fixation site is shown pulled back such that a distal end 5701 of catheter is offset from both tip electrode 1518 and ring electrode 1520 to expose electrodes 1518 and 1520 for electrical testing. Electrical testing may be conducted via contact surfaces 1532 and 1534 of extension 1530 since connector rings 1522 and 1524 of lead 1510 are covered up by guide catheter 5700 when electrodes 1518 and 1520 are exposed. FIG. 17 shows a pace/sense analyzer box 5780 electrically coupled to contact surfaces 1532 and 1534 via lead wires 5732 and 5734, respectively. In another embodiment of a lead, a distal portion 5200 of lead body 1512 may include a defibrillation electrode, which would also be exposed for defibrillation threshold testing via a contact surface on extension 1530. In yet another embodiment, only contact surface 1532 is included on extension 1530 so that tip electrode 1518 is tested in a unipolar mode; such unipolar embodiments were described above in conjunction with FIG. 12C. Once electrical testing confirms an effective position of electrodes 1518 and 1520, catheter 5700 is removed. FIG. 17 further illustrates a length L of extension 1530 sufficient to maintain a hands-on control of lead 1510 while guide catheter 5700 is being removed, i.e. lead may always be grasped outside venous access site 5770, either via extension 1530, proximally to a proximal end 5702 of guide catheter 5700, or directly on lead body 1512, distally to distal end 5701 of guide catheter 5700, while guide catheter 5700 is pulled out from the venous system. It should be noted that guide catheter 5700 may alternately be used to deliver a lead having an extension, such as extension 1530, into a right atrium 5760 or to a left side of the heart via a coronary sinus 5740; in either case, an extension, such as extension 1530, would function in a manner similar to that described herein above. Once catheter 5700 has been removed, proximal portion 1515 of lead 1510 may be engaged in sleeve assembly 5100 as will be described below in conjunction with FIG. 18.

FIG. 18 is a plan view illustrating one method according to the present invention of engaging proximal portion 1515 of lead 1510 with connector sleeve assembly 5100, wherein a lead introducer 5150 is inserted in distal end 5105 of sleeve assembly 5100 to slightly expand a distal opening of central lumen 5118 of sleeve assembly 5100 for insertion of proximal end 1515 into sleeve assembly 5100. As illustrated in FIG. 18, extension 1530 has been inserted into sleeve assembly 5100 by passing proximal end 1538 of extension 1530 through introducer 5150 and advancing extension 1530 through sleeve assembly 5100 until proximal end 1538 exits proximal opening 5109 of pin terminal 5102. Extension 1530 may be pulled in the direction indicated by arrow 5160 until proximal portion 1515 is engaged within sleeve assembly 5100. In an alternate embodiment of the present invention an introducer is not required for engagement of proximal portion 1515 in sleeve assembly 5100.

FIG. 19 is a plan view of lead introducer 5150. Introducer 5150, a generally tubular, thin-walled structure, includes an inner lumen 5152 having a wide opening 5154 at a distal end and a narrower, generally circular opening 5156 at a proximal end. Introducer 5150 is preferably formed from a lubricious material, such as PTFE. In one embodiment, introducer 5150 may be fabricated from a short section, for example 1 to 2 inches, of thin-walled lubricious tubing having an inner diameter slightly larger than the outer diameter of lead 1510 and an outer diameter approximately equal to or just slightly greater than the diameter of sleeve assembly lumen 5118. The tubing may be cut lengthwise along a distance on the order of one half the tubing length. In this manner, a widened, flared opening 5154 is created at a distal end of introducer 5150 that allows easy insertion of extension 1530 and proximal portion 1515 of lead 1510.

FIG. 20 is a plan view of the fully assembled lead 1510 and connector sleeve assembly 5100. FIG. 20 illustrates severing section 1526 protruding proximally from proximal opening 5109 of connector terminal 5102 as an indication that proximal portion 1515 of lead is engaged within sleeve assembly 5100 so that connector rings 1522 and 1524 (FIG. 11) are aligned with contacts 5114 and 5116 (FIG. 14), respectively. Complete insertion of proximal end 1515 into sleeve assembly 5100 is accomplished by applying traction to extension 1530 while pushing sleeve assembly 5100 over proximal lead end 1514. According to one embodiment of the present invention, an amount of force required to completely pull proximal end 1515 into sleeve 5100, such that lead connector rings 1522 and 1524 engage with sleeve assembly contacts 5114 and 5116, is on the order of less than approximately 5 pounds, more preferably on the order of approximately 2 pounds or less. Complete insertion may be verified by visualization of severing section, according to various marks described herein above in conjunction with FIG. 11, and/or by tactile feedback arising from the alignment of connector rings 1522 and 1524 with contacts 1514 and 1516 as rings 1522 and 1524 snap into place. This alignment may also make an audible "snapping" or "clicking" sound that verifies proper engagement has been made between connector rings 1522 and 1524 and contacts 1514 and 1516, respectively.

FIG. 20 further illustrates a severing at severing section 1526 according to arrow 5162 by which extension 1530 is removed up to a point flush with the tip of pin terminal 5102. Upon removal of extension 1530, lead 1510 and sleeve assembly 5100 may be connected to a medical device.

Figure 21:
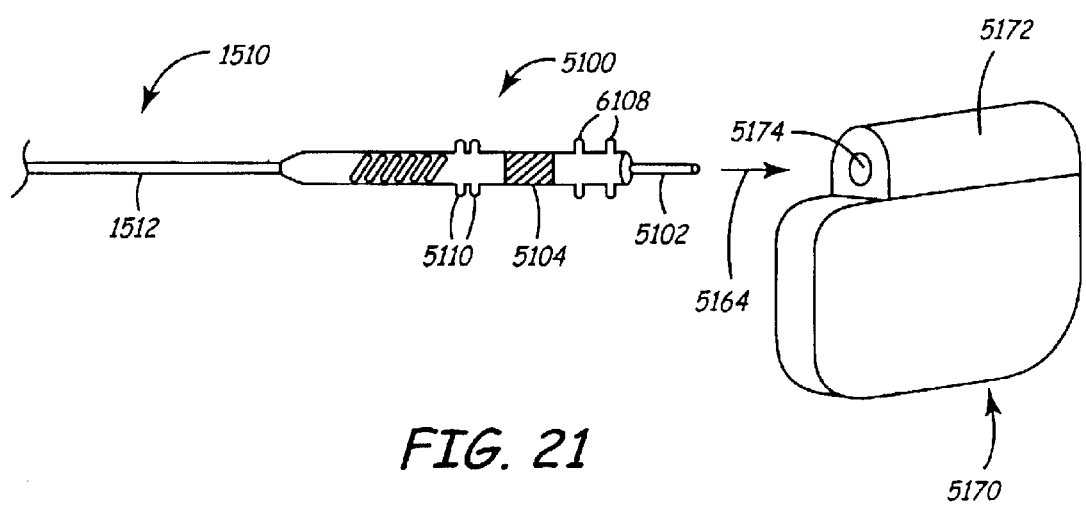
FIG. 21 is a perspective view of the engaged lead and sleeve assembly being inserted into an exemplary medical device.

FIG. 21 is a perspective view of the assembled lead 1510 and sleeve assembly 5100 being inserted into an exemplary medical device 5170. Device 5170 may be for example, a pacemaker, ICD, implantable monitor, neurological stimulator, or muscle stimulator. Device 5170 includes a connector block 5172 having at least one connector port 5174. Connector port 5174 may conform to an IS-1 connection standard or any other industry standard. The outer dimensions of sleeve assembly 5100 are sized to fit connector port 5174.

The fully assembled lead 1510 and sleeve assembly 5100 may be inserted into connector port 5174 as indicated by arrow 5164. Once inserted, external sealing rings 5108 and 5110 will form fluid-tight seals with the inner surface of port 5174 and pin terminal 5102 and ring terminal 5104 will be aligned with corresponding terminals within port 5174 thus providing electrical connection between lead 1510 and device 5170. The corresponding terminals within port 5174 may be in the form of set-screws, therefore, according to one embodiment of the present invention, walls formed about axial through bores 5107 and 5111 of pin terminal 5102 and ring terminal 5104, respectively, must be rigid enough to withstand a force imposed by the set-screws without being crushed. Such set-screw terminals are commonly employed and are well known to those skilled in the art of implantable medical device connectors.

Figure 22:
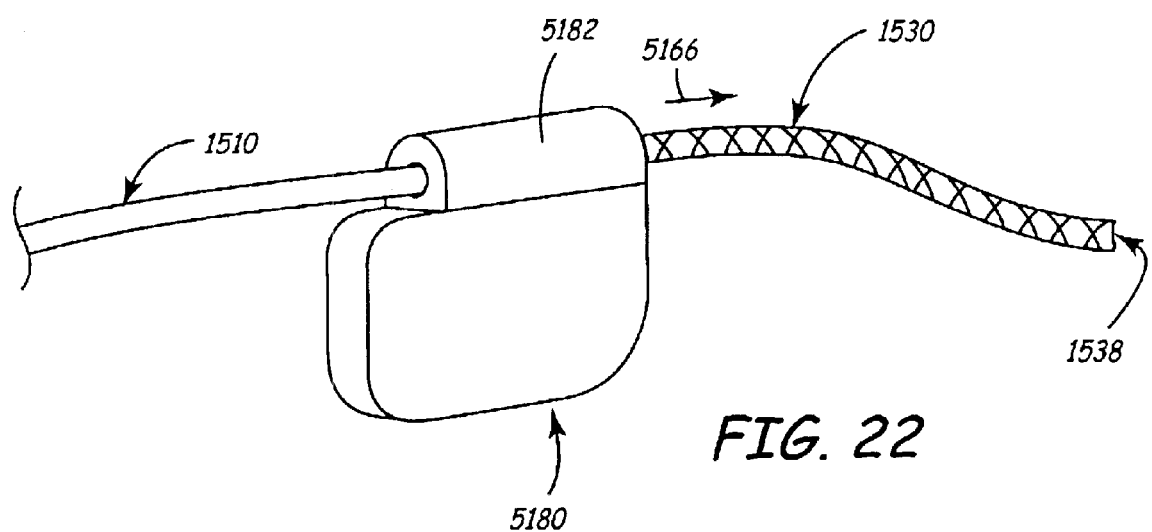
FIG. 22 is a perspective view of a lead being inserted into an exemplary medical device.

FIG. 22 is a perspective view of a lead 1510 being inserted into an exemplary medical device 5180. Device 5180 may be for example, a pacemaker, ICD, implantable monitor, neurological stimulator, or muscle stimulator. As illustrated in FIG. 22, device 5180 includes a connector block 5182 having at least one connector port 5184, which includes a first opening 5186 and a second opening (not shown). Connector port 5184 is adapted to engage proximal portion 1515 (FIG. 11 and FIG. 12A) of lead 1510 without a need for sleeve assembly 5100. Such a connector port is described by Bischoff et al. in commonly assigned U.S. Pat. No. 5,843,141, which is incorporated herein in its entirety. In a manner similar to that described above for inserting lead 1510 into sleeve assembly 5100, proximal end 1538 of extension 1530 may be inserted into first opening 5186 and threaded out second opening where it may be grasped to pull proximal portion 1515 of lead into port 5184 per arrow 5166. Once proximal portion 1515 is fully engaged in port 5184, extension may be severed in a manner similar to that described above.

Thus, a medical lead connection system has been described that allows a small diameter lead to be implanted using a guide catheter and then be connected to a connector port of a medical device. Specific embodiments of the lead and connector assembly system provided by the present invention have been described. Alternative lead and connector assembly designs may include inventive aspects described herein in order to provide a medical lead connection system. As such, the above disclosure should be considered exemplary, rather than limiting, with regard to the following claims.

What is claimed is:

1. A method for implanting a medical electrical lead, comprising:
  delivering a plurality of lead electrodes formed along a distal portion of a lead body to an implant site via a guiding catheter;
  pulling the guiding catheter proximally over the lead body to expose the plurality of electrodes and thereby covering a plurality of connector rings, the plurality of connector rings formed along a proximal portion of the lead body and each coupled to a respective electrode of the plurality of electrodes by a respective conductor of a plurality of conductors extending within the lead body; and temporarily electrically connecting an external device, for electrical testing of the plurality of electrodes, a plurality of temporary contacts positioned along an extension joined to, and extending proximally from a proximal end of the proximal portion of the lead body, the plurality of temporary contacts each electrically coupled to a respective connector ring of the plurality of connector rings by the respective conductor of the plurality of conductors, which further extend from the lead body into the extension.

2. The method of claim 1, further comprising:

inserting the extension and the proximal portion of the lead body through a first opening of a connector lumen until the extension and a visual marker, positioned in proximity to the proximal end of the proximal portion of the lead body, extends proximally from a second opening of the lumen; and severing the extension from the proximal portion of the lead body.

3. The method of claim 2, wherein the connector lumen is included in a connector sleeve body.

4. The method of claim 2, wherein the connector lumen is included in a device connector block.

5. An implantable medical electrical system, comprising a medical electrical lead, the lead comprising:

an elongated lead body including a proximal end;

an elongated lead extension extending proximally from the proximal end of the lead body;

an elongated conductor extending within the lead body and the extension;

a connector ring mounted about the lead body in proximity to the proximal end and electrically coupled to the conductor; and a temporary contact surface mounted on the extension and electrically coupled to the conductor.

6. The system of claim 5, wherein the lead extension includes a severing section positioned in proximity to the lead body proximal end, the severing section serving for subsequent removal of the lead extension.

7. The system of claim 6, wherein the lead extension includes a visual marker positioned to mark the severing section in order to distinguish the severing section from a remainder of the lead extension.

8. The system of claim 5, wherein the lead extension includes a visual marker positioned in proximity to the lead body proximal end.

9. The system of claim 5, wherein the lead further comprises an elongate member having a relatively low extensibility, the member extending within the lead extension.

10. The system of claim 9, wherein the elongate member is formed of a polyester fiber.

11. The system of claim 9, wherein the elongate member further extends within the lead body.

12. The system of claim 5, wherein:

the lead conductor comprises a plurality of conductors;

the lead connector ring comprises a plurality of connector rings each coupled to a one of the plurality of conductors; and the lead temporary contact surface comprises a plurality of temporary contact surfaces each coupled to a one of the plurality of conductors.

13. The system of claim 5, wherein a maximum diameter of the lead extension is less than or equal to a minimum diameter of the lead body.

14. The system of claim 5, wherein the lead connector ring includes a tapered outer diameter.

15. The system of claim 5, further comprising a connector sleeve assembly, the connector sleeve assembly comprising:

a generally tubular sleeve body forming a lumen for engaging the lead proximal end and the lead connector ring; and a pin connector member extending from a proximal end of the sleeve body and Including an axial through bore having a proximal opening, the axial through bore being approximately aligned with the sleeve body lumen; and wherein the lead extension extends proximally from the proximal opening of the pin connector axial through bore when the sleeve body lumen engages the lead proximal end and the lead connector ring.

16. The system of claim 15, wherein the lead extension includes a visual marker positioned in proximity to the lead body proximal end, the visual marker extending proximally from the proximal opening of the pin connector axial through bore when the sleeve body lumen engages the lead proximal end and the lead connector ring.

17. The system of claim 15, wherein the lead extension includes a severing section positioned In proximity to the lead body proximal end, the severing section extending proximally from the proximal opening of the pin connector axial through bore when the sleeve body lumen engages the lead proximal end and the lead connector ring.

18. The system of claim 15, wherein the pin connector member further includes a terminal pin, the terminal pin including a rigid wall formed about a portion of the axial through bore, the rigid wall resistant to set-screw crush forces.

19. The system of claim 15, wherein the pin connector member further includes a terminal pin and a spring contact, the spring contact integrally formed in the pin connector member and axially offset, distally, from the pin terminal.

20. The system of claim 15, wherein the generally tubular sleeve body includes a ring connector member, the ring connector member including an axial through bore forming a portion of the sleeve body lumen.

21. The system of claim 20, wherein the sleeve body ring connector member further Includes a terminal ring, the terminal ring including a rigid wall formed about a portion of the ring connector member axial through bore, the rigid wail resistant to set-screw crush forces.

22. The system of claim 20, wherein the sleeve body ring connector member further includes a terminal ring and a spring contact, the spring contact integrally formed in ring connector member and axially offset, distally, from the terminal ring.

23. A method for implanting a medical electrical lead, comprising:

delivering a lead electrode formed along a distal portion of a body of the lead to an implant site via a guiding catheter;

pulling the guiding catheter proximally over the lead body to expose the electrode for electrical testing and thereby covering a connector ring formed along a proximal portion of the lead body, the connector ring being electrically coupled to the electrode via an elongate conductor extending within the lead body; and temporarily electrically connecting an external device for the electrical testing to a temporary contact positioned along an extension of the lead, the extension extending proximally from the proximal portion of the lead body and the temporary contact being electrically coupled to the connector ring by the conductor which further extends into the extension.

24. The method of claim 23, further comprising:
 inserting the extension and the proximal portion of the lead body through a first opening of a connector lumen until the extension extends proximally from a second opening of the lumen; and
 severing the extension from the proximal portion of the lead body.

25. The method of claim 24, wherein the connector lumen is included in a connector sleeve body.

26. The method of claim 24, wherein the connector lumen is included in a device connector block.

* * * * *